US005888516A

United States Patent [19]
Jansen et al.

[11] Patent Number: 5,888,516
[45] Date of Patent: Mar. 30, 1999

[54] RECOMBINANT PAPILLOMAVIRUS VACCINES

[75] Inventors: Kathrin U. Jansen, Ft. Washington; James C. Cook, III, Lansdale; Hugh A. George, Schwenksville; Kathryn J. Hofmann, Collegeville; Joseph G. Joyce, Lansdale; Ernest Dale Lehman, Lansdale; Henry Z. Markus, Wyncote; Mark Rosolowsky, Doylestown; Loren S. Schultz, Harleysville, all of Pa.

[73] Assignee: Merck & Co. Inc., Rahway, N.J.

[21] Appl. No.: 969,523

[22] Filed: Oct. 22, 1997

Related U.S. Application Data

[63] Continuation of Ser. No. 440,800, May 15, 1995, abandoned, which is a continuation-in-part of Ser. No. 242,794, May 16, 1994, abandoned.

[51] Int. Cl.$^6$ .............................. A61K 39/12; C12N 7/04
[52] U.S. Cl. ...................... 424/204.1; 435/69.3; 435/236
[58] Field of Search ........................ 424/204.1; 435/69.3, 435/69.1, 235.1, 236

[56] References Cited

U.S. PATENT DOCUMENTS

| | | | |
|---|---|---|---|
| 5,437,951 | 8/1995 | Lowy et al. | 435/69.1 |
| 5,618,536 | 4/1997 | Lowy et al. | 424/192.1 |

FOREIGN PATENT DOCUMENTS

| | | |
|---|---|---|
| WO 93/02184 | 4/1993 | WIPO . |
| WO 94/00152 | 1/1994 | WIPO . |
| WO 94/05792 | 3/1994 | WIPO . |
| WO 94/20137 | 9/1994 | WIPO . |

OTHER PUBLICATIONS

Browne, H.M. et al. "Analysis of the L1 Gene Product of Human Papillomavirus Type 16 by Expression in a Vaccinia Virus Recombinant" J. Gen. Virol. (1988) vol. 69, pp. 1263–1273.

Doorbar, J. et al. "Identification of Proteins Encoded by the L1 and L2 Open Reading Frames of Human Papillomavirus 1a"; Jour. of Virology, Sep. 1987, vol. 67, No. 9, pp. 2793–2799.

Hagensee, M.E. et al, "Self–Assembly of Human Papillomavirus Type 1 Capsids by Expression of the L2 Protein Alone or by Coexpression to the L1 and L2 Capisid Proteins"; Jour. of Virology, Jan. 1993, vol. 67. No. 1, pp. 315–322.

Kirnbauer, R. "Papillomavirus L1 major capsid protein self–assemblies into virus–like particles that are highly immunogenic", Proc. Natl. Acad. Sci, vol. 89, pp. 12180–12184, Dec. 1992.

LeCann, P. et al. "Self–assembly of human papillomavirus type 16 capsids by expression of the L1 protein in insect cells", FEMS Microbiology Letters, 117 (1994) pp. 269–274.

Lin, Y. et al. "Effective Vaccination against Papilloma Development by Immunization with L1 or L2 Structural Protein of Cottontail Rabbit Papillomavirus", Virology, vol. 187, (1992) pp. 612–619.

Rose, R. et al. "Expression of Human Papillomavirus Type 11 L1 Protein in Insect Cells: In Vivo and in Vitro Assembly of Viruslike Particles", Jour. of Virology, Apr. 1993, pp. 1936–1944.

Steele J. et al. "Humoral Assays of Human Sera to Disrupted and Nondisrupted Epitopes of Human Papillomavirus Type 1", Virology, Vo. 174, (1990) pp. 388–398.

Strike, D. et al. "Expression in *Escherichia coli* of Seven DNA Fragments Comprising the Complete L1 and L2 Open Reading Frames of Human Papillomavirus Type 6b and Localization of the Common Antigen Region", J. Gen. Virol. (1989) Vo. 70, pp. 543–555.

Zhou, J. et al. "Synthesis and assembly of infectious bovine papillomavirus particles in vitro", Jour. Gen. Virology (1993), vol. 74, pp. 763–768.

Zhou, J. et al. "Expression of Vaccinia Recombinant HPV 16 L1 and L2 ORF Proteins in Epithelial Cells is Sufficient for Assembly of HPV Virion–like Particles", Virology, vol. 185 (1991) pp. 251–257.

Zhou, J. et al. "Increased antibody responses to human papillomavirus type 16 L1 protein expressed by recombinant vaccinia virula lacking serine protease inhibitor genes", Jour. Gen. Virology, (1990) vol. 71, pp. 2185–2190.

Hjorth, R. et al. Journal of Virological Methods, vol. 5, pp. 151–158, 1982.

Lowe, R. S. et al. Journal of Infectious Diseases, vol. 176, pp. 1141–1145, 1997.

Jansen, K. U. et al. Vaccine, vol. 13, pp. 1509–1514, 1995.

Zhou, J. et al. Virology, vol. 194, p. 210–218, 1993.

Carter, et al., "Expression of Human Papillomavirus Proteins in Yeast Saccharomyces Cerevisiae", Virology, 182, pp. 513–521 (1991).

Kirnbauer, et al., "Efficient Self–Assembly of Human Papillomavirus Type 16 L1 and L1–L2 into Virus–Like Particles", J. of Vir., Dec. 1993, pp. 6929–6936, vol. 67, No. 12.

*Primary Examiner*—Mary E. Mosher
*Attorney, Agent, or Firm*—Joanne M. Giesser; Jack L. Tribble

[57] ABSTRACT

Recombinant expression vectors encoding the L1 and L2 proteins of papillomavirus, methods of making and using the recombinant proteins and purified virus-like particles comprised of the recombinant proteins are provided.

3 Claims, 15 Drawing Sheets

2150-2-3 (*MATa, leu2, ade1*)

↓ Select ura⁻ on FOA plates

U9 (*MATa, leu2, ade1, ura3*)

↓ Transform with *mnn9::URA3* disruption cassette

1372 (*mnn9, leu2, ade1*)

↓ Select ura⁻ on FOA plates

1372-ura3 (*mnn9, leu2, ura3, ade1*)

↓ Transform with *his3::URA3* disruption cassette

1372-his3 (*mnn9, leu2, his3, ade1*)

↓ Transform with *prb1::HIS3* disruption cassette strain 1558 (*MATa, leu2, mnn9, prb1, ade1*)

FIG. 6

| RECOMBINANT STRAIN | PV CODING SEQUENCE(S) | YEAST HOST STRAIN[a] |
|---|---|---|
| 1582 | CRPV L1 | 1569 |
| 1583 | CRPV L2 | 1538 |
| 1603 | CRPV L1 + L2 (2-PLASMID SYSTEM) | 1592 |
| 1606 | CRPV L1 + L2 | 1569 |
| 1609 | CRPV L1 + L2 | BJ5462 |
| 1644 | HPV 6a L1 | 1558 |
| 1670 | HPV 6a L1 + L2 | 1558 |
| 1678 | HPV 16 L1 | 1558 |
| 1679 | HPV 16 L1 + L2 | 1558 |

FIG.9

```
        Scheme 2   Scheme 3
200 —    —
116 —
 97 —
 66 —                     ← L1
 55 —

RECOMBINANT PAPILLOMAVIRUS VACCINES

CROSS-REFERENCE TO RELATED APPLICATIONS

This is a continuation of application Ser. No. 08/440,800, filed May 15, 1995, now abandoned, which is a continuation-in-part of application Ser. No. 08/242,794, filed May 16, 1994, now abandoned.

FIELD OF THE INVENTION

Recombinant expression vectors encoding the L1 and L2 proteins of papillomavirus, methods of making the recombinant proteins and methods of using the recombinant proteins are provided.

BACKGROUND OF THE INVENTION

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16 and 18 cause epithelial dysplasia of the genital mucosa and are associated with the majority of in situ and invasive carcinomas of the cervix, vagina, vulva and anal canal. HPV6 and HPV11 are the causative agents for more than 90% of all condyloma (genital warts) and laryngeal papillomas. The most abundant subtype of HPV type 6 is HPV6a.

Immunological studies in animals have shown that the production of neutralizing antibodies to papillomavirus antigens prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model.

Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunologic data suggest that most of the L2 protein is internal to the L1 protein. The L2 proteins are highly conserved among different papillomaviruses, especially the 10 basic amino acids at the C-terminus. The L1 ORF is highly conserved among different papillomaviruses.

The L1 and L2 genes have been used to generate vaccines for the prevention and treatment of papillomavirus infections in animals. Zhou et al., (1991; 1992) cloned HPV type 16 L1 and L2 genes into a vaccinia virus vector and infected CV-1 mammalian cells with the recombinant vector to produce virus-like particles (VLP).

Bacterially-derived recombinant bovine papillomavirus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV6 L1, HPV 11 L1, HPV16 L1, HPV18 L1, HPV31 L1 or HPV16 L2 ORFs have been used to infect insect SF9 cells and produce L1 and L2 proteins. Western blot analyses showed that the baculovirus-derived L1 and L2 proteins reacted with antibody to HPV 16. The baculovirus derived L1 forms VLPs.

Carter et al., (1991) demonstrated the production of HPV 16 L1 and HPV 16 L2 proteins by recombinant strains of *Saccharomvces cerevisiae*. Carter et al. also demonstrated the production of HPV6b L1 and L2 proteins. The HPV6b L1 protein was not full-length L1 protein. The recombinant proteins were produced as intracellular as well as secreted products. The recombinant L1 and L2 proteins were of molecular weights similar to the native proteins. When the proteins were expressed intracellularly, the majority of the protein was found to be insoluble when the cells were lysed in the absence of denaturing reagents. Although this insolubility may facilitate purification of the protein, it may hamper analysis of the native epitopes of the protein.

Recombinant proteins secreted from yeast were shown to contain yeast-derived carbohydrates. The presence of these N-linked oligosaccharides may mask native epitopes. In addition, the secreted recombinant proteins may contain other modifications, such as retention of the secretory leader sequence.

It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein.

The present invention is directed to the production of recombinant papillomavirus proteins having the immunity conferring properties of the native papillomavirus proteins as well as methods for their production and use. The present invention is directed to the production of a prophylactic and possibly therapeutic vaccine for papillomavirus infection. The recombinant proteins of the present invention are capable of forming virus-like particles. These VLP are immunogenic and prevent formation of warts in an animal model. The present invention uses the cottontail rabbit papillomavirus (CRPV) and HPV type 6 (subtype 6a) as model systems.

SUMMARY OF THE INVENTION

Recombinant expression vectors encoding the L1 and L2 proteins of papillomavirus, methods of making the recombinant proteins and methods of using the recombinant proteins are provided.

BRIEF DESCRIPTION OF THE DRAWINGS

FIG. 6 Immunoblots of CRPV L1 , L2, and L1+L2 proteins expressed in yeast. Panel (A): Expression of CRPV L1 as measured by reactivity with anti-CRPV L1 antiserum. Panel (B): Expression of CRPV L2 as measured by reactivity with anti-CRPV L2 antiserum. Lane 1, molecular weight markers in kDa (Amersham Rainbow™ Markers, 14,300–200,000 daltons); Lane 2, BJ5462 containing the CRPV L1 expression vector; Lane 3, strain 1569 containing the CRPV L2 expression vector; Lanes 4 and 5, two isolates of strain 1569 cotransformed with two plasmids for expression of CRPV L1 and CRPV L2; Lanes 6–8, three isolates of strain 1569 containing single vector for coexpression of CRPV L1 and L2 proteins; Lanes 9 and 10, two isolates of BJ5462 containing single vector for coexpression of CRPV L1 and L2 proteins. The position of migration of L1 and L2 are marked on the right axis of the appropriate panel. FIG. 6 is

FIG. 9 outlines major steps in a purification procedure.

FIGS. 13 and 14 are SDS/PAGE analyses of purified VLP.

DETAILED DESCRIPTION OF THE INVENTION

Figure 1:
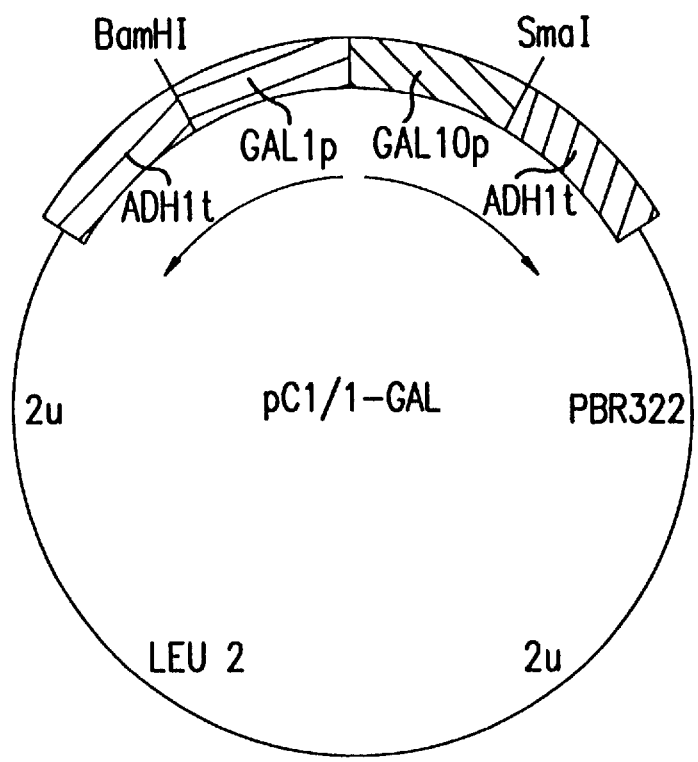
FIG. 1 shows bidirectional yeast expression vector used to express papillomavirus L1 and/or L2 capsid proteins.
Figure 2A:
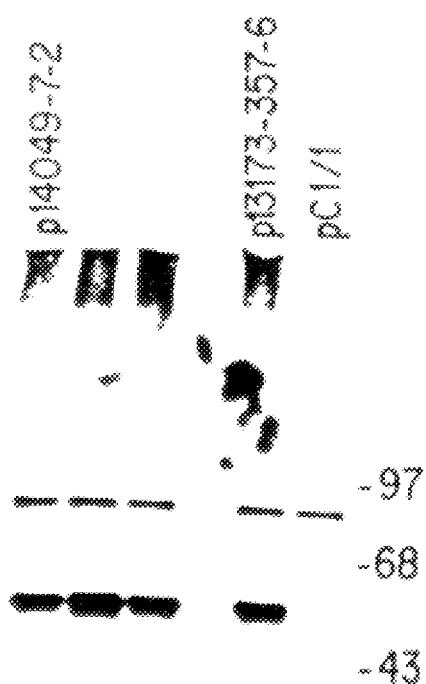
FIG. 2 shows expression of HPV6a L1 in yeast (immunoblot).
Figure 2B:
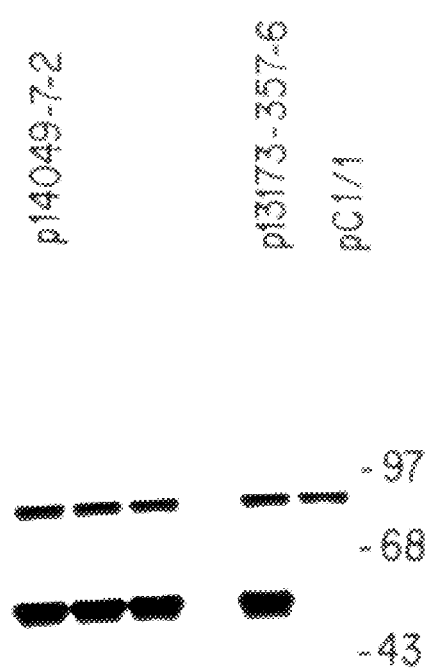
Figure 3:
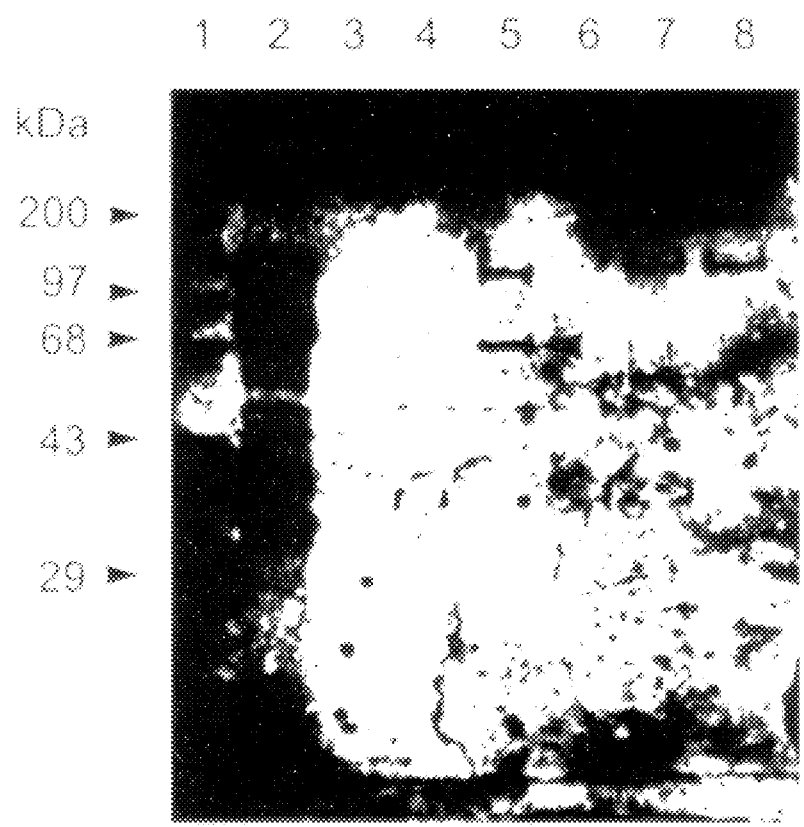
FIG. 3 shows expression of HPV6a L2 in yeast. Immnunoblot of HPV6a L2 expressed in yeast; lane. 1, molecular weight markers; lane 2, trpE-L2 fusion protein expressed in E. coli as positive control; lane 4, HPV6a L1 expressed in yeast as negative control; lane 5, HPV6a L2 expressed in yeast (for experimental details see text).
Figure 4:
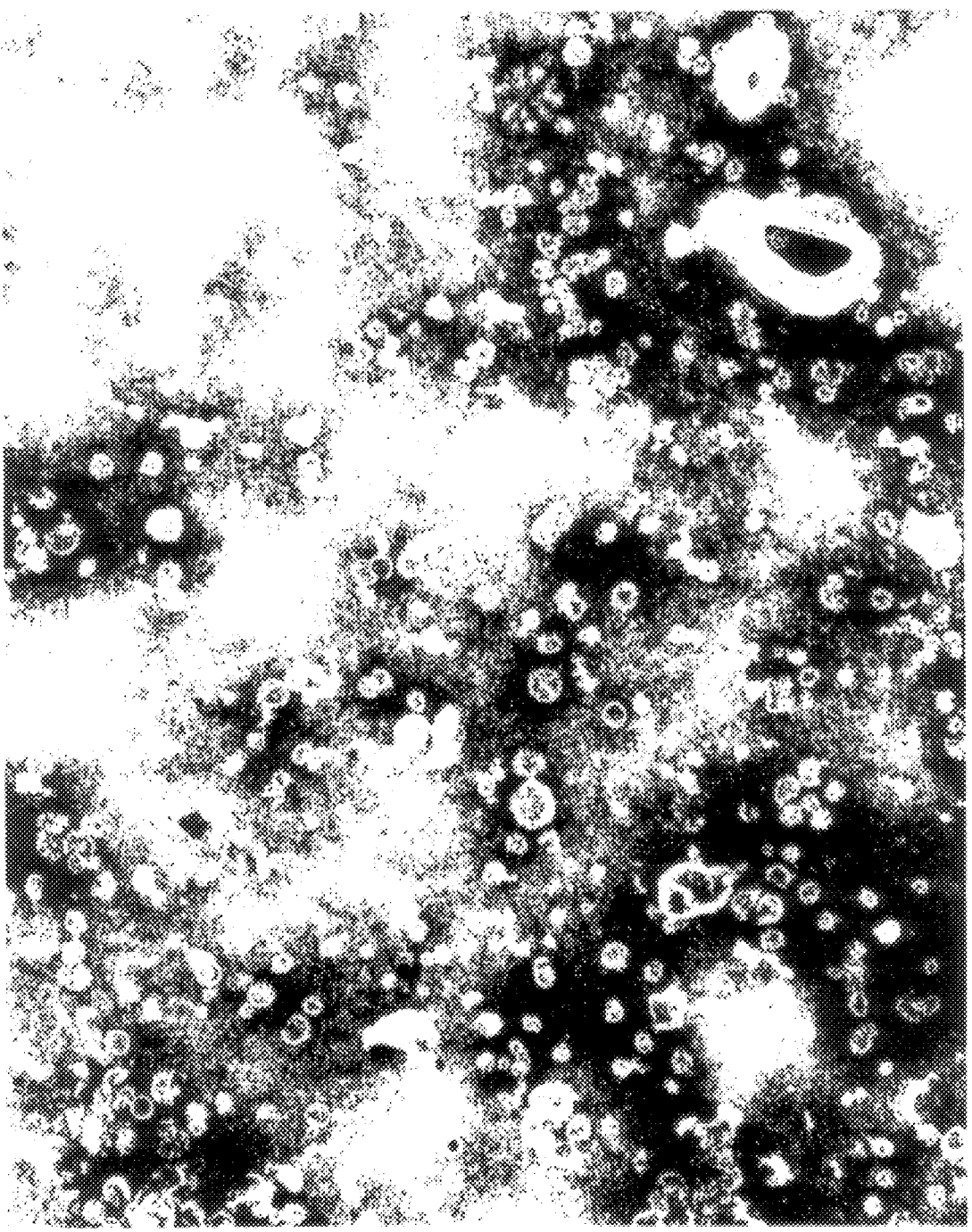
FIG. 4 is an electron micrograph of HPV6a L1 VLPs expressed in yeast.
Figure 5A:
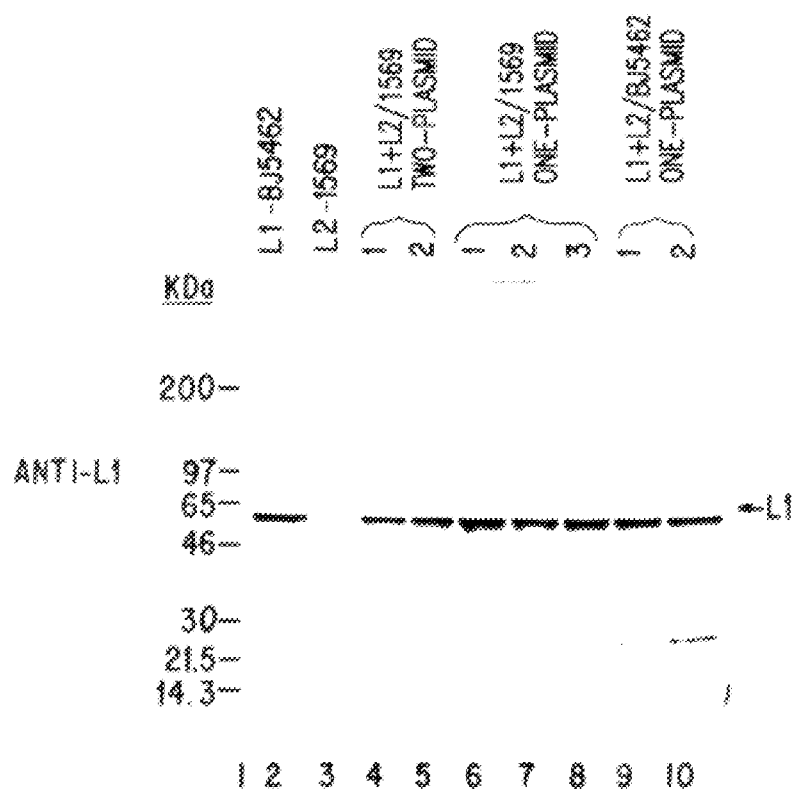
FIG. 5 is an electron micrograph of HPV6a L1 l/L2 VLPs expressed in yeast.
Figure 5B:
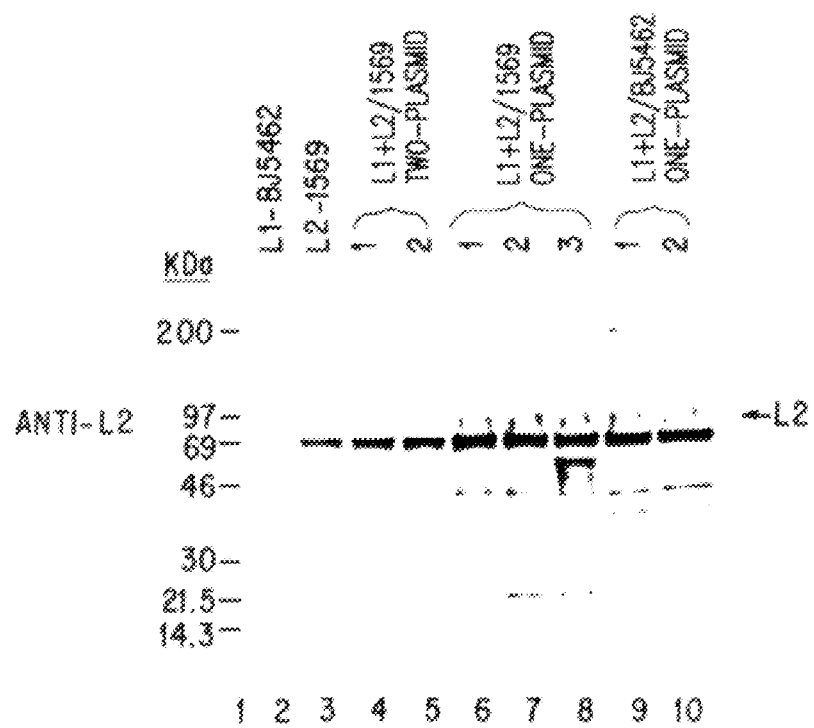

Methods, compositions and processes for the prevention, characterization, detection and treatment of papillomavirus (PV) infection are provided. The methods are based on the production of recombinant L1 or recombinant L2 or recombinant L1 and L2 proteins in yeast. The recombinant proteins are capable of mimicking the conformational neutralizing epitopes of native PV. The recombinant L1 or L1 and L2 proteins may also be capable of forming virus-like particles (VLP). The compositions of the invention include but are not limited to recombinant DNA molecules encoding the L1 or L2 or L1 and L2 proteins, the recombinant proteins either alone or in combination with other recombinant proteins, VLP comprised of at least one recombinant protein, fragments of the recombinant proteins, pharmaceutical compositions comprising the recombinant proteins, vaccine compositions comprising the recombinant proteins, antibodies to the recombinant proteins or VLP, immunogenic compositions comprising at least one recombinant protein, and diagnostic kits comprising the recombinant DNA molecules or the recombinant proteins. The processes of the present invention include but are not limited to the process of producing a recombinant protein comprising the transformation of an appropriate yeast host cell with a recombinant DNA molecule, cultivating the transformed yeast under conditions that permit the expression of the DNA encoding the recombinant protein, and purifying the recombinant protein. The processes of the present invention also include the administration of the recombinant protein, recombinant protein compositions or VLP to an animal, including but not limited to humans. Appropriate host cells include, but are not limited yeast strains of the genera Saccharomyces, Pichia, Kluyvermvces, Schizosaccharomvces and Hansenula.

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital and respiratory mucosa. HPV types 16 and 18 cause epithelial dysplasia of the genital tract and are associated with the majority of in situ and invasive carcinomas of the cervix, vagina, vulva and anal canal. HPV6 and HPV 11 cause the majority of genital warts and laryngeal papillomas.

Immunological studies in animals have shown that the production of neutralizing antibodies to papillomavirus capsid proteins prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model.

Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated El to E7 and L1 and L2, where "E" denotes early and "L" denotes late. L1 and L2 code for virus capsid proteins. The early (E) genes are associated with functions such as viral replication and transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis.

The production of HPV 16 L1 , HPV16 L2, and HPV type 6 L1 proteins by recombinant strains of *Saccharomyces cerevisiae* has been reported. It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein.

The present invention is directed to the production of recombinant papillomavirus proteins having the immunity conferring properties of the native papillomavirus proteins as well as methods for their production and use. The present invention is particularly directed to the production of a prophylactic vaccine for papillomavirus infection. The present invention is exemplified by cottontail rabbit papillomavirus (CRPV) and human papillomavirus type 6 (HPV type 6 or HPV6) as model systems. The exemplification does not limit the scope of the invention, which includes other types and subtypes of papillomavirus (PV), including but not limited to HPV type 11, HPV type 16 and HPV type 18 as well as HPV subtype 6a and HPV subtype 6b.

Pharmaceutically useful compositions comprising the proteins or VLP may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or VLP. Such compositions may contain proteins or VLP derived from more than one type of HPV.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 µg to about 250 µg.

The pharmaceutical compositions may be provided to the individual by a variety of routes such as subcutaneous, topical, oral, mucosal, and intramuscular.

The vaccines of the invention comprise recombinant proteins or VLP that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The therapeutically effective amount may vary according to the type of PV. The vaccine may be administered in single or multiple doses.

The methods of the present invention make possible the formulation of subviral vaccines for preventing PV infection. Using the methods, either monovalent or multivalent PV vaccines may be made. For example, a monovalent HPV type 16 vaccine may be made by formulating recombinant HPV 16 L1 protein or L2 protein or L1 and L2 proteins. Alternatively, a multivalent HPV vaccine may be formulated by mixing L1 or L2 or L1 and L2 proteins or VLP from different HPV types.

The recombinant proteins and VLP of the present invention may be used in the formulation of immunogenic compositions. Such compositions, when introduced into a suitable host, are capable of inducing an immunologic response in the host.

The recombinant proteins and VLP may be used to generate antibodies. The term "antibody" as used herein includes both polyclonal and monoclonal antibodies, as well as fragments thereof, such as, Fv, Fab and F(ab)2 fragments that are capable of binding antigen or hapten.

The recombinant proteins, VLP and antibodies of the present invention may be used to serotype HPV infection and HPV screening. The recombinant proteins, VLP and antibodies lend themselves to the formulation of kits suitable for the detection and serotyping of HPV. Such a kit would comprise a compartmentalized carrier suitable to hold in close confinement at least one container. The carrier would further comprise reagents such as recombinant HPV protein or VLP or anti-HPV antibodies suitable for detecting a variety of HPV types. The carrier may also contain means for detection such as labeled antigen or enzyme substrates or the like.

The recombinant proteins and VLP of the present invention are also useful as molecular weight and molecular size markers.

The following examples are provided to further define the invention without, however, limiting the invention to the particulars of these examples.

EXAMPLE 1

Preparation of Yeast Strain U9

*Saccharomyces cerevisiae* strain 2150-2-3 (MATa, leu2-04, ade1, cir°) was obtained from Dr. Leland Hartwell (University of Washington, Seattle, Wash.). Cells of strain 2150-2-3 were propagated overnight at 30° C. in 5 mL of YEHD medium (Carty et al., *J. Ind. Micro.* 2 (1987) 117–121). The cells were washed 3 times in sterile, distilled water, resuspended in 2 mL of sterile distilled water, and 0.1 mL of cell suspension was plated onto each of six 5-fluoro-orotic acid (FOA) plates in order to select for ura3 mutants (Cold Spring Harbor Laboratory Manual for Yeast Genetics). The plates were incubated at 30° C. The medium contained per 250 mL distilled water: 3.5 g, Difco Yeast Nitrogen Base without amino acids and ammonium sulfate; 0.5 g 5-Fluoro-orotic acid; 25 mg Uracil; and 10.0 g Dextrose.

The medium was sterilized by filtration through 0.2 µm membranes and then mixed with 250 mL of 4% Bacto-Agar (Difco) maintained at 50° C., 10 mL of a 1.2 mg/n L1 mL solution of adenine, and 5 mL of L-leucine solution (180 mg/50 mL). The resulting medium was dispensed at 20 mL per petri dish.

After 5 days of incubation, numerous colonies had appeared. Single colonies were isolated by restreaking colonies from the initial FOA plates onto fresh FOA plates which were then incubated at 30° C. A number of colonies from the second set of FOA plates were tested for the presence of the ura3 mutation by replica-plating onto both YEHD plates and uracil-minus plates. The desired result was good growth on YEHD and no growth on uracil-minus medium. One isolate (U9) was obtained which showed these properties. It was stored as a frozen glycerol stock (strain #325) at −70° C. for later use.

EXAMPLE 2

Preparation of a Vector for disruption of the Yeast MNN9 gene

In order to prepare a vector for disruption of the MNN9 gene, it was necessary to first clone the MNN9 gene from *S. cerevisiae* genomic DNA. This was accomplished by standard Polymerase Chain Reaction (PCR) technology. A 5' sense primer and 3' antisense primer for PCR of the full-length MNN9 coding sequence were designed based on the published sequence for the yeast MNN9 gene (Zymogenetics: EPO Patent Application No. 88117834.7, Publication No. 0-314-096-A2). The following oligodeoxy-nucleotide primers containing flanking HindIII sites (underlined) were used:

sense primer: 5'-CTT A<u>AA GCT T</u>AT GTC ACT TTC TCT TGT ATC G-3'(SEQ ID NO:1)

antisense primer: 5'-TGA T<u>AA GCT</u> TGC TCA ATG GTT CTC TTC CTC-3'(SEQ ID NO:2).

The initiating methionine codon for the MNN9 gene is highlighted in bold print. The PCR was conducted using genomic DNA from *S. cerevisiae* strain JRY188 as template, Taq DNA polymerase (Perkin Elmer) and 25 cycles of amplification (94° C. 1 min., 37° C. 2 min., 72° C. 3 min.). The resulting 1.2 kbp PCR fragment was digested with HindIII, gel-purified, and ligated with HindIII-digested, alkaline-phosphatase treated pUC13 (Pharmacia). The resulting plasmid was designated p1183.

In order to disrupt the MNN9 gene with the yeast URA3 gene, the plasmid pBR322-URA3 (which contains the 1.1 Kbp HindIII fragment encoding the *S. cerevisiae* URA3 gene subcloned into the HindIII site of pBR322) was digested with HindIII and the 1.1 kbp DNA fragment bearing the functional URA3 gene was gel-purified, made blunt-ended with T4 DNA polymerase, and then ligated with PmlI-digested plasmid p1183 (PmlI cuts within the MNN9 coding sequence). The resulting plasmid p1199 contains a disruption of the MNN9 gene by the functional URA3 gene.

EXAMPLE 3

Construction of U9-derivative strain 1372 containing disruption of MNN9 gene

For disruption of the MNN9 gene in strain U9(#325), 30 μg of plasmid p 1199 were digested with HindIII to create a linear mnn9::URA3 disruption cassette. Cells of strain 325 were transformed with the HindIII-digested p1199 DNA by the spheroplast method (Hinnen et al., 1978, Proc. Natl. Acad. Sci. USA &5:1929–1933) and transformants were selected on a synthetic agar medium lacking uracil and containing 1.0M sorbitol. The synthetic medium contained, per liter of distilled water: Agar, 20 g; Yeast nitrogen base w/o amino acids, 6.7 g; Adenine, 0.04 g; L-tyrosine, 0.05 g; Sorbitol, 182 g; Glucose, 20 g; and Leucine Minus Solution #2, 10 ml. Leucine Minus Solution #2 contains per liter of distilled water: L-arginine, 2 g; L-histidine, 1 g; L-Leucine, 6 g; L-Isoleucine, 6 g; L-lysine, 4 g; L-methionine, 1 g; L-phenylalanine, 6 g; L-threonine, 6 g; L-tryptophan, 4 g.

The plates were incubated at 30° C. for five days at which time numerous colonies had appeared. Chromosomal DNA preparations were made from 10 colonies and then digested with EcoRI plus HindIII. The DNA digests were then evaluated by Southern blots (J. Sambrook et al., *Molecular Cloning: A Laboratory Manual,* 2nd edition, Cold Spring Harbor Laboratory Press, 1989) using the 1.2 kbp HindIII fragment bearing the MNN9 gene (isolated from plasmid p1199) as a probe. An isolate was identified (strain #1372) which showed the expected DNA and shifts on the Southern blot as well as the extreme clumpiness typically shown by MNN9 mutants.

EXAMPLE 4

Construction of a Vector for Disruption of Yeast HIS3 Gene

In order to construct a disruption cassette in which the *S. cerevisiae* HIS3 gene is disrupted by the URA3 gene, plasmid YEp6 (K. Struhl et al., 1979, Proc. Natl. Acad. Sci., USA 76:1035) was digested with BamHI. The 1.7 kbp BamHI fragment bearing the HIS3 gene was gel-purified, made blunt-ended with T4 DNA polymerase, and ligated with pUC 18 which had been previously digested with BamHI and treated with T4 DNA polymerase. The resulting plasmid (designated p L1 I501 or pUCl8-HIS3) was digested with NheI (which cuts in the HIS3 coding sequence), and the vector fragment was gel-purified, made blunt-ended with T4 DNA polymerase, and then treated with calf intestine alkaline phosphatase. The URA3 gene was isolated from the plasmid pBR322-URA3 by digestion with HindIII and the 1.1 kbp fragment bearing the URA3 gene was gel-purified, made blunt-ended with T4 DNA polymerase, and ligated with the above pUC18-HIS3 NheI fragment. The resulting plasmid (designated pUC L1 I8-his3::URA3 or p1505) contains a disruption cassette in which the yeast HIS3 gene is disrupted by the functional URA3 gene.

EXAMPLE 5

Construction of Vector for Disruption of Yeast PRB1 Gene by the HIS3 Gene

Plasmid FP8ΔH bearing the *S. cerevisiae* PRB1 gene was provided by Dr. E. Jones of Carnegie-Mellon Univ. (C. M. Moehle et al., 1987, *Genetics* 115:255–263). It was digested with HindIII plus XhoI and the 3.2 kbp DNA fragment bearing the PRB1 gene was gel-purified and made blunt-ended by treatment with T4 DNA polymerase. The plasmid pUC18 was digested with BamHI, gel-purified and made blunt-ended by treatment with T4 DNA polymerase. The resulting vector fragment was ligated with the above PRB1 gene fragment to yield the plasmid pUC18- PRB1 Plasmid YEp6, which contains the HIS3 gene, which was digested with BamHI. The resulting 1.7 kbp BamHI fragment bearing the functional HIS3 gene was gel-purified and then made blunt-ended by treatment with T4 DNA polymerase. The pUC18-PRB1 was digested with EcoRV plus NcoI which cut within the PRB1 coding sequence and removes the protease B active site and flanking sequence. The 5.7 kbp EcoRV-NcoI fragment bearing the residual 5' and 3'-portions of the PRB1 coding sequence in pUC 18 was gel-purified, made blunt-ended by treatment with T4 DNA polymerase, dephosphorylated with calf intestine alkaline phosphatase, and ligated with the blunt-ended HIS3 fragment described above. The resulting plasmid (designated pUC18-prbl::HIS3, stock #1245) contains the functional HIS3 gene in place of the portion of the PRB1 gene which had been deleted above.

EXAMPLE 6

Construction of a U9-related Yeast Strain containing disruptions of both the MNN9 and PRB1 Genes The U9-related strain 1372 which contains a MNN9 gene disruption was described in Example 3. Clonal isolates of strain 1372 were passaged on FOA plates to select ura3 mutants. A number of ura3 isolates of strain 1372 were obtained, and one isolate (strain 12930-190-S1-1) was selected for subsequent disruption of the HIS3 gene. The pUC18-his3::URA3 gene disruption vector (p1505) was digested with XbaI plus EcoRI to generate a linear his3::URA3 disruption cassette and used for transformation of strain 12930–190-S1-1 by the lithium acetate method (*Methods in Enzymology*, 194:290 (1991). Ura$^+$ transformants were selected on synthetic agar medium lacking uracil, restreaked for clonal isolates on the same medium, and then replica-plated onto medium lacking either uracil or histidine to screen for those isolates that were both Ura$^+$ and His$^-$. One isolate (strain 12930-230-1) was selected for subsequent disruption of the PRB1 gene. The PRB1 gene disruption vector (pUC L1 I8-prbl::HIS3, stock #1245) was digested with SacI plus XbaI to generate a linear prbl::HIS3 disruption cassette and used for transformation of strain 12930-230-1 by the Lithium Acetate method. His$^+$ transformants were selected on agar medium lacking histidine and restreaked on the same medium for clonal isolates. Genomic DNA was prepared from a number of the resulting His$^+$ isolates, digested with EcoRI, and then electrophoresed on 0.8% agarose gels. Southern blot analyses were then performed using a radio-labeled 617 bp probe for the PRB1 gene which had been prepared by PCR using the following oligodeoxynucleotide primers:

5'TGG TCA TCC CAA ATC TTG AAA 3'(SEQ ID NO:3)

5'CAC CGT AGT GTT TGG AAG CGA 3'(SEQ ID NO:4)

Eleven isolates were obtained which showed the expected hybridization of the probe with a 2.44 kbp prbl::HIS3 DNA fragment. This was in contrast to hybridization of the probe with the 1.59 kbp fragment for the wild-type PRB1 gene. One of these isolates containing the desired prbl::HIS3 disruption was selected for further use and was designated strain #1558.

EXAMPLE 7

Construction of a Vector for Disruption of Yeast PEP4 Gene

The *S. cerevisiae* PEP4 gene was cloned from a yeast genomic library in the following manner. *E. coli* cells containing the yeast genomic library pLS101 (Schultz and Friesen, 1983, *J. Bacteriol.* 155: 8–14)) were propagated overnight in 5 mL of LB medium containing 100 μg/mL ampicillin. From this culture, 10$^{-4}$ and 10$^{-5}$ dilutions were plated on LB plus ampicillin plates. Colony plates lifts were prepared using nitrocellulose filters. A 600 bp probe for the yeast PEP4 gene was prepared by PCR using Taq DNA polymerase, total plasmid DNA from the pLS101 yeast library, and the following oligodeoxynucleotide primers designed based on the published DNA sequence for PEP4 (C. A. Woolford et al., *Mol. Cell. Biol.* 6:2500 (1986)).

Sense Primer: 5'-GAG GCT ACC AGC GAG CCG GGC-3'(SEQ ID NO:5)

Antisense Primer: 5'-GGC CAG TGG GCC AAC AGG TTC-3'(SEQ ID NO:6).

The PCR was conducted with 25 cycles of amplification (94° C. 1 min., 37° C. 2 min., 72° C. 3 min.). The PCR probe was gel-purified, radio-labeled, and hybridized with the above colony filters. Several colonies were positive for hybridization with the PEP4 probe and were restreaked on LB plus ampicillin plates for single colonies. Plasmid DNA was prepared by the alkaline-SDS lysis (Sambrook et al., supra) from several of the isolates and digested with BamHI. The expected 14 kbp vector band and 6.9 kbp PEP4 insert band were observed. Upon double digestion with EcoRI plus XhoI, the expected 1.5 kbp band for PEP4 was observed. One isolate (strain #860) showing the expected results was selected for further use. Plasmid DNA from strain #860 was digested with BamHI and the 6.9 kbp BamHI DNA fragment carrying the chromosomal PEP4 gene was subcloned into the BamHI site of pUC13 to yield the plasmid p890. The plasmid p890 was then digested with NcoI (which cuts within the PEP4 coding sequence), gel-purified, made blunt-ended by treatment with T4 DNA polymerase, and ligated with the 1.1 kbp blunt-ended fragment bearing the functional URA3 gene (prepared as in Example 2). The resulting plasmid containing the PEP4 gene disrupted by the URA3 gene was designated pUC13-pep4::URA3 (strain #906).

EXAMPLE 8

Construction of Yeast Strain #1569 which is Derivative of Strain U9 Containing both prb1 and pep4 Mutations In order to disrupt the HIS3 gene in strain U9, the disruption vector pUC18-his3::URA3 was digested with EcoRI plus XbaI and then used to transform strain U9 by the lithium acetate method. Ura$^+$ transformants were selected on agar medium lacking uracil and restreaked on the same medium for clonal isolates. A number of the resulting Ura$^+$ isolates were then replica-plated onto agar medium lacking either uracil or histidine and screened for those that were both Ura$^+$ and His$^-$. One isolate (strain #1524) was selected for subsequent disruption of the PRB1 gene. The PRB1 gene disruption vector pUC18-prbl::HIS3 was digested with SacI plus XbaI and then used for transformation of strain #1524 by the lithium acetate method. His$^+$ transformants were selected on agar medium lacking histidine and restreaked for clonal isolates on the same medium. Genomic DNA was prepared from a number of the His$^+$ isolates and evaluated by Southern blot hybridization with a radio-labeled PRB1 probe. One of the isolates (strain #1537) showing the desired disruption of the PRB1 gene by HIS3 (i.e., prb1::HIS3) was selected for subsequent disruption of the PEP4 gene. Strain #1537 was passaged on FOA plates in order to obtain ura3 isolates and one isolate (strain #1541) was selected for further use.

In order to disrupt the PEP4 gene in strain #1541, the PEP4 gene disruption vector pUC13-pep4::URA3 was digested with XhoI to generate a linear pep4::URA3 disruption cassette and used for transformation of strain #1541 by the lithium acetate method. Ura$^+$ transformants were selected on uracil-minus agar medium and streaked for clonal isolates on the same medium. Genomic DNA was prepared from a number of the Ura+transformants and evaluated by Southern blots using a radio-labeled probe for the PEP4 gene. One isolate (strain #1569) showing the desired disruption of the PEP4 gene by the URA3 gene was selected for further use.

EXAMPLE 9

Construction of CRPV L1 Expression Vector

The CRPV L1 gene was amplified by PCR from plasmid pLAII which contains the complete CRPV viral genome (Dr. Peter Howley, NCI) using Vent polymerase (New England Biolabs, Inc.); 35 cycles of amplification (94° C., 1 min; 50° C., 1 min; 72° C., 2 min) and the following oligonucleotide primers which contain flanking BglII sites (underlined) were used:

sense primer: 5'- GA<u>A GAT CT</u>T CAA AAC AAA ATG GCA GTG TGG CTG TCT AC-3'(SEQ ID NO:7)

antisense primer: 5'-GA<u>A GAT CT</u>T TAT TAA GTA CGT CTC TTG CGT T L1 TAG-3'(SEQ ID NO:8)

The sense primer introduces a yeast non-translated leader sequence immediately upstream of the CRPV L1 initiating methionine codon (highlighted in bold print). The 1.6 kb L1 PCR product was digested with BglI L1 1, gel-purified and subcloned into the Bgl II site of vector pSP72 (Promega) to yield the plasmid pSP72-CRPV-L1 (p12930-314-4-1).

One subclone was sequenced completely and found to be different in 4 nucleotides from the published CRPV L1 sequence. The changes do not result in amino acid changes. The L1 gene was cut out of pSP72-CRPV-L1 as a Bgl II fragment and subcloned into the unique BamHI site located between the yeast GAL10 promoter and ADH1 transcriptional terminator in the yeast expression vector pC1/1-GAL10p-ADH1t which contains the GAL10 promoter from YEp52 (Broach et al., *Exp. Manipulation of Gene Expression*, 1983, 83:81–116) and ADH1 transcriptional terminator in a pC1/1 vector backbone). The resulting plasmid was designated p12930-323-6-1.

EXAMPLE 10

Construction of CRPV L2 Expression Vector

The CRPV L2 gene was amplified by PCR using Vent polymerase (New England Biolabs, Inc.) from plasmid pLAII after digesting the plasmid with SalI, gel purifying the 7.9 Kb fragment and ligating it with itself. Thirty-five cycles of amplification (90° C., 1 min; 50° C., 1 min; 72° C., 2 min) and oligonucleotide primers which contain flanking EcoRI sites (underlined) were used:

sense primer: 5'-G<u>GA ATT C</u>AC AAA ACA AAA TGG TTG CAC GGT CAC GAA AAC-3'(SEQ ID NO:9)

antisense primer: 5'-G<u>GA ATT C</u>TT ATT CTG CGT AGA CAG CCA CAC TG-3'(SEQ ID NO: 10)

The sense primer introduces a yeast non-translated leader sequence immediately upstream of the CRPV L1 initiating methionine codon (highlighted in bold print). The 1.5 kb PCR product was digested with EcoRI, gel-purified and subcloned into the EcoRI site of the bidirectional promoter vector pUC18-GAL1p-GAL10p containing the divergent yeast GAL1/GAL10 promoter. This vector contains a unique BamHI site between the GAL1 1 promoter and a first copy of the ADH1 transcription terminator, unique EcoRI and SmaI sites located between the GAL10 promoter, and a second copy of the ADH1 transcriptional terminator. The resulting expression cassette is carried on a 1.4 kb SphI fragment. One clone (p12930-295-2-2) containing the desired L2 insert adjacent to the GAL10 promoter was completely sequenced and shown to contain 6 nucleotide changes from the published sequence, 4 of which result in amino acid changes. Sequence analysis of the original template DNA confirmed that the changes were also present in pLAII and not introduced by the PCR. The pUC18-GAL1p-GAL10p vector containing the L2 gene was cut with SphI and the 2.9 kb fragment harboring the ADH1t-GAL1p-GAL10p-L2-ADH1t expression cassette was ligated with the large SphI fragment of the yeast shuttle vector pC1/1. The resulting plasmid was designated p12930-323-2-3 (pC1/1-GAL1p-GAL10p-CRPV-L2).

EXAMPLE 11

Expression of CRPV L1 and CRPV L2 Capsid Protein in Yeast

Plasmids p12930-323-6-1 and pl2930-323-2-3 (pC1/1-GAL10p-CRPV/L1 and pC1/1-GAL1p-GAL10p-CRPV/L2) were used to transform *S. cerevisiae* strains #1569, BJ5462 [E. W. Jones, *Methods in Enzymology* 194 (1991) 428–453] and BJ1995 [Jones, ibid.]. Clonal isolates were grown at 30L1 ° C in YEHD medium containing 2% galactose for 48–72 hours. After harvesting the cells, the cell pellets were broken with glass beads, Triton X-100 was added to 0.5% final concentration and the resulting cell lysates were evaluated for the expression of CRPV L1 and L2 by immunoblot analyses. Samples containing 40 µg of total cellular protein were electrophoresed on 12% Tris-Glycine gels (Novex) under reducing and denaturing conditions and electroblotted onto PVDF membranes (Novex). CRPV L1 and L2 proteins were detected using polyclonal rabbit anti-L1 or anti-L2 antisera (gift of Dr. John Kreider, Hershey Medical Center) as primary antibodies and protein A coupled to horseradish peroxidase (Amersham, Inc.) as the secondary antibody. The membranes were processed using the chemiluminescent ECL ™ Detection Kit (Amersham, Inc.). A 55–61 kDa L1 protein band was detected in all samples harboring the L1 expression plasmid and a ~90 kDa L2 protein band was detected in all samples from yeast clones harboring the L2 expression plasmid.

No signal was detected in samples derived from yeast clones harboring the L1 expression plasmid with anti-L2 antisera or vice versa.

EXAMPLE 12

A. Purification of Recombinant CRPV L1 Capsid Protein

All steps were performed at 4° C. unless specified. Cells, stored at −70° C., were thawed and suspended in an equal volume of "L1 Buffer" (20 mM sodium phosphate, pH 7.2, 100 mM NaCl, 1.7 mM EDTA). Protease inhibitors PMSF and Pepstatin A were added to the slurry to final concentrations of 2 mM and 1.7 μM respectively. Cells were lysed by 10 passes in a microfluidizer. The lysate was clarified by centrifugation at 5000×g for 10 minutes. The supernatant was layered on top of a 5 cm cushion of 45% sucrose (w/v) in L1 buffer, and L1 was pelleted by centrifugation at 100,000×g for 4 hours. The pellet was resuspended in 1/10 volume of L1 buffer and clarified by centrifugation at 5000×g for 10 minutes. Tween-80 was added to the supernatant to a final concentration of 0.01 % (v/v) and the supernatant was fractionated at room temperature by size-exclusion chromatography on a 1700 ml column (5 cm ID) of Sephacryl S-1000 resin (Pharmacia). Running buffer for this column was 10 mM sodium phosphate, pH 7.2, 150 mM NaCl, 0.01% (v/v) Tween-80. Fractions containing immunoreactive material by immuno-dot blot were pooled and concentrated to ⅙ volume by ultrafiltration using an Amicon stirred cell with a 76 mm diameter YM- 100 flat-sheet membrane (100,000 MWCO). The product was sterile filtered through a Millex-GV 0.22 μm membrane (Millipore). Purified CRPV L1 Capsid Protein was adsorbed to aluminum hydroxide at a concentration of 100 μg/ml.

B. Characterization of Recombinant CRPV L1 Capsid Protein

The identity of the final product was confirmed by Western blotting and by N-terminal sequence analysis. Purity was assessed by SDS/PAGE with Coomassie and silver staining, and by Solution Sieving Capillary Electrophoresis (SSCE) with optical detection at 215 nm. The preparation was 75% pure L1 by SSCE.

EXAMPLE 13

Purification of Recombinant CRPV L2 Capsid Protein

All steps were performed at 4° C. unless specified. Cells, stored at −70° C., were thawed and suspended in an equal volume of "L1 Buffer" (20 mM sodium phosphate, pH 7.2, 100 mM NaCl, 1.7 mM EDTA). Protease inhibitors PMSF and Pepstatin A were added to the slurry to final concentrations of 2 mM and 1.7 $\mu$M respectively. Cells were lysed by 10 passes in a microfluidizer. The lysate was clarified by centrifugation at 5000×for 10 minutes. The supernatant was layered on top of a 5 cm cushion of 45% sucrose (w/v) in L1 buffer, and L2 was pelleted by centrifugation at 100,000×g for 4 hours. The pellet was resuspended in 1/10 volume of L1 buffer. The resuspended pellet was clarified by centrifugation at 5000×g for 10 minutes. Tween-80 was added to the supernatant to a final concentration of 0.01% (v/v) and the supernatant was fractionated at room temperature by size-exclusion chromatography on a 1700 ml column (5 cm ID) of Sephacryl S-1000 resin (Pharmacia). Running buffer for this column was 10 mM sodium phosphate, pH 7.2, 150 mM NaCl, 0.01% (v/v) Tween-80. Fractions containing immunoreactive material by immuno-dot blot were pooled. Pooled fractions were analyzed by SDS/PAGE (silver) and by Western blotting.

EXAMPLE 14

A. Purification of Recombinant CRPV L1 Capsid Protein-Scheme 1

Cells stored at −70° C., were thawed and suspended in an equal volume of Breaking buffer (20 mM sodium phosphate, pH 7.2, 100 mM NaCl, 1.7 mM EDTA). Protease inhibitors PMSF and Pepstatin A were added to the slurry to final concentrations of 2 mM and 1.7 $\mu$M respectively. Cells were lysed by 10 passes in a microfluidizer. The lysate was clarified by centrifugation at 5000×g for 10 minutes. The supernatant was layered on top of a 5 cm cushion of 45% sucrose (w/v) in L1 buffer, and L1 was pelleted by centrifugation at 100,000×g for 4 hours. The pellet was resuspended in 1/10th volume of L1 buffer. The resuspended pellet was clarified by centrifugation at 5000×g for 10 minutes. Tween-80 was added to the supernatant to a final concentration of 0.01 % and the supernatant was fractionated at room temperature by size-exclusion chromatography on a 1700 ml column (5 cm ID) of Sephacryl S- 1000 resin (Pharmacia). Running buffer for this column was 10 mM sodium phosphate, pH 7.2, 150 mM NaCl, 0.01 % Tween-80. Fractions containing immunoreactive material by immunodot blot assay were pooled and concentrated to 1/6th volume by ultrafiltration using an Amicon stirred cell with a 76 mm diameter YM-100 flat-sheet membrane (100,000 MWCO). The product was sterile filtered through a Millex-GV 0.22 $\mu$m membrane (Millipore).

B. Characterization of Recombinant CRPV L1 Capsid Protein

The identity of the final product was confirmed by Western blotting and by N-terminal sequence analysis. Purity was assessed by SDS/PAGE with Coomassie and silver staining, and by Solution Sieving Capillary Electrophoresis (SSCE) with optical detection at 215 nm. L1 was 75% pure by SSCE. Electron microscopy showed that VLP in the 50–55 nm diameter size range were present.

C. Analytical Size-Exclusion HPLC

To assay for VLP, samples were fractionated according to size by size-exclusion chromatography. Chromatography was performed with a Perkin-Elmer Series 410 Biopump HPLC with an ISS 100 autoinjector fitted with a 200 microliter injection loop. The column was a TSK-gel G5000PW, 7.5×600 mm (TOSOHAAS, Montgomeryville, Pa.). To monitor elution of protein from the column, optical detection at 280 nm was accomplished with a Perkin-Elmer LC-235 diode array detector. The mobile phase was 0.5 M NaCl in 10 mM sodium phosphate buffer, pH 7.2. The flow rate was 0.5 mL/min, and one milliliter fractions were collected. Column calibration was performed with protein standards from Sigma as well as recombinant hepatitis B surface antigen (Recombivax, Merck & Co., West Point, Pa.). Detection of antigen in fractions collected during elution is accomplished by immunodot blot assay.

D. Immunodot Blot Assay

A 10 microliter sample of each fraction was applied to a strip of PVDF membrane (Immobilon-P, Millipore Corp., Bedford, Mass.) which was pre-wetted and placed on dampened blotting paper. The sample was allowed to soak into the membrane, and the membrane was placed in a Blocking Solution (5% (w/v) of non-fat dry milk dissolved in 0.15M NaCl, 0.02% (w/v) sodium azide, and 0.01M sodium phosphate, pH 7.2) and incubated at room temperature with gentle agitation for a minimum of three hours. Blocking solution was decanted and replaced with primary antibody solution.

Primary antibody used varied depending on the antigen to be detected:

CRPV L1 was probed with rabbit anti-CRPV serum "late response" (Biodesign International, Kennebunk, Me.). CRPV L2 was probed with rabbit anti-CRPV L2 serum. HPV6a L1 was probed with monoclonal antibody MAB 837 (Chernicon International, Inc., Temecula, Calif.). HPV6a L2 was probed with mouse anti-HPV6a L2-trpE fusion serum.

Visualization of the immune complexes was by standard methods using a second antibody conjugated to alkaline phosphatase and the chromogenic substrate NBT/BCIP.

E. Solution Sieving Capillary Electrophoresis (SSCE)

Samples of CRPV VLP (~0.2 milligram/milliliter) were heated for 15 minutes at 100° C. in 1% 2-mercaptoethanol and 1% (w/v) SDS. The sample was applied electrokinetically along with a reference marker, mellitic acid, to a silica fused capillary, 42 cm (22 cm to detector) ×0.05 mm I.D., pre-equilibrated with 10 lumen volumes of 0.1N NaOH, water, and ProSort sieving reagent (Applied Biosystems, Foster City, Calif.). A separation voltage of 300 volts/cm was applied using an Applied Biosystems Model 270A-HT CE instrument. Elution of sample was monitored by absorbance at 215 nm, and data was collected using Nelson Turbochrom 3 software.

F. Preparation of Vaccine from Recombinant CRPV L1 Capsid Protein

Purified CRPV L1 Capsid Protein was adsorbed to Al(OH)3 at a concentration of 100 µg/ml.

EXAMPLE 15

Protection Against Papilloma Development Caused by CRPV by Vaccination with Yeast Derived CRPV L1 VLPs 5 New Zealand White rabbits were immunized intramuscularly with either 135 mg of L1 VLPs (75% pure, see Example 17) adsorbed to alum or 1100 mg recombinant hepatitis B surface antigen (99% pure) adsorbed to aluminum hydroxide as a negative control. Animals received 2 more boosts over 8 weeks before they were challenged with CRPV 10 days after the last boost. Sera taken before immunization, at each boost, and before challenge were analyzed by an L1-VLP specific ELISA. An indirect ELISA assay was used to determine serum antibody responses to yeast-expressed CRPV L1 VLPs. The antigens used in the ELISA were CRPV L1 VLPs expressed in insect cells with a recombinant baculovirus essentially as described by Christensen et al. (J. Virol. 64:3151–3156, 1990; J. Gen. Virol. 75:2271–2276 (1994). Goat anti-rabbit IgG-alkaline phosphatase was used as second antibody and p-nitrophenyl phosphate as substrate (Kirkegaard and Perry Labs., Inc.). Absorbance was measured at 405 nm. The titer was determined by endpoint-dilution (3-fold dilutions of sera starting at 1:100) and was considered positive if the L1 -specific absorbance exceeded the mean absorbance readings plus 2 standard deviations of rabbit preimmune sera. Exact titers were calculated from these data using the SOFTmax program version 2.3 (Molecular Devices Inc., Menlo Park, Calif.).

Anti-L1 i VLP antibody titers were present 4 weeks after the first immunization, and they increased with each additional boost. Control animals were negative. 6 weeks after CRPV challenge the vaccinated animals were wart-free in 15 out of 15 sites (1:2 diluted or 1:12 diluted virus stock) while the control animals show wart formation in 12 out of 15 sites (1:2 diluted virus) or 9 out of 15 (1:12 diluted virus). After 15 weeks, the vaccinated animals were still wart-free.

Virus neutralization assays were performed (essentially according to method of Christensen et al., 1991, *Virology* 181:572–579) by mixing rabbit sera with CRPV and subsequently challenging rabbits with the treated CRPV. The standard for determining neutralizing antibody was complete virus neutralization (3/3 sites negative for wart formation). Sera from the 5 vaccinated animals and 5 control animals were analyzed. Sera collected after 1 dose of CRPV L1 VLPs contained antibodies which completely neutralized undiluted virus in 80% of rabbits (4/5). After 2 or 3 doses of CRPV L1 VLPs 100% of rabbits (5/5) had virus neutralizing antibodies. Control sera did not show any virus neutralizing activity. Depending on final titers sera of selected vaccinated animals could be diluted between 10–1000 fold and were still 100% neutralizing.

To test whether the neutralizing antibody response was specific for native CRPV L1 VLPs , one immune serum was chosen and incubated with nitrocellulose squares which had been coated with either native or denatured yeast-derived CRPV L1 VLPs. Nitrocellulose squares (1 cm$^2$) were coated with either native or denatured (reduced and alkylated with iodoacetic acid in 8M urea) yeast-expressed CRPV L1 VLPs. Native or denatured yeast extracts were used as controls. Rabbit immune serum was incubated serially 4 times with the nitrocellulose squares for 8–14 hours at 40° C., before it was tested in the virus-neutralization assay as described above. Only native CRPV L1 VLPs were able to absorb the antibodies responsible for neutralizing CRPV, while denatured or control yeast proteins did not absorb these antibodies. In addition, native CRPV L1 VLPs also removed the ELISA reactivity to CRPV L1 VLPs expressed in insect cells (data not shown).

EXAMPLE 16

Construction of Vector for Coexpression of CRPV L1/L2 from a Single Plasmid

Plasmid pSP72-CRPV-L1 (pl2930-314-4-1) was digested with BglII and the 1.5 kbp BgII fragment bearing the CRPV L1 ORF with a yeast 5'-nontranslated leader was gel-purified. Plasmid pl2930-323-2-3 (pC1/1-GAL1p-GAL10p-CRPV-L2) was digested with BamHI which cuts between the GAL1 promoter and the ADH1 transcriptional terminator. The linear vector fragment was gel-purified and then ligated with the aforementioned CRPV-L1 BglII fragment to yield the plasmid pl2930-366-1-2 (pC1/1-GAL1/10p-CRPV/L1+L2). This resulting plasmid contains the CRPV-L1 ORF under control of the GAL1 promoter and the CRPV-L2 ORF under control of the GAL10 promoter.

EXAMPLE 17

Construction of Vector for Coexpression of CRPV L1/L2 from Two Plasmids

The pUC18-GAL1p-GAL10p vector containing the L2 gene was cut with SphI and the 2.9 kb fragment harboring the ADH1t-GAL1p-GA10p-L2-ADG1t expression cassette was gel-purified and made blunt-ended by treatment with T4 DNA polymerase. The yeast shuttle vector YEp24 [Botstein et al., *Gene* 8:17 (1979)] was digested with BamHI, made blunt-ended by treatment with T4 DNA polymerase, dephosphorylated with calf intestine alkaline phosphatase and then ligated with the above blunt-ended L2 expression cassette to yield the plasmid p1594.

EXAMPLE 18

Coexpression of CRPV L1 and L2 in Yeast

Plasmid p12930-366-1-2 (pC1/1 -GAL1/10-CRPV/L1+L2) was used to transform *S. cerevisiae* strains #1569 and BJ5462 (one plasmid system) and the resulting transformants were selected on leucine-minus synthetic agar medium. In a parallel experiment, strain 1569 was cotransformed with the pC 1/1-GAL10p-CRPV-L1 expression vector p12930-323-6-1 plus the YEp24-GAL10p-L2 expression vector pl594 (two plasmid system) and the resulting transformants containing both vectors were selected on synthetic agar medium lacking both leucine and uracil. Clonal isolates for both the one plasmid system and two plasmid system were grown at 30° C. in YEHD complex medium containing 2% galactose for 48–72 hours. After harvesting the cells, the cell pellets were broken with glass beads. Triton X-100 was added to 0.5% final concentration and cell lysates were analyzed for the expression of CRPV L1 and L2 by i L1 immunoblot analysis. Samples containing 50 μg of total cellular protein were electrophoresed on 8–16% Tris-Glycine gradient gels (Novex) under reducing and denaturing conditions and electroblotted onto PVDF membranes (Novex). CRPV L1 and L2 proteins were detected using polyclonal rabbit anti-L1 or anti-L2 antisera (gift of Dr. John Kreider, Hershey Medical Center) as primary antibodies and protein A coupled to horseradish peroxidase (Amersham, Inc.) as the secondary antibody. The membranes were processed using the chemiluminescent ECL™ Detection Kit (Amersham, Inc.). A 55–61 kDa L1 protein band and a ~90 kDa L2 protein band was detected in all samples from yeast clones harboring the L1+L2 expression plasmid. No signal for L2 was detected in samples derived from yeast clones harboring the expression plasmid for L1. No signal for L1 was detected in samples from cells containing only the L2 expression vector.

EXAMPLE 19

Purification of CRPV L1 and CRPV L1+L2 VLPs for EM studies

The yeast expressed CRPV L1 and CRPV L1 and L2 proteins were partially purified and concentrated for electron microscopy (EM) studies. One to 1.5 liters of YEHD medium containing 2% galactose were inoculated with *S. cerevisiae* strain #1569 or BJ5462 transformed with the L1+L2 coexpression vector pl2930-366-1-2 (pC1/1-GAL1/10p-CRPV/L1+L2) and grown at 30° C. for 48–72 hours. In a parallel experiment, cells of strain #1569 co-transformed with the GAL10p-CRPV-L1 expression vector p12930-323-6-1 plus the YEp24-GAL10p-L2 plasmid p1594 were grown in a similar fashion. The cells were harvested and cell pellets frozen at −70° C. All following steps were performed at 4° C. Cell pellets were thawed and suspended in an equal volume of "L1 buffer" (20 mM sodium phosphate, pH 7.2, 100 mM NaCl, 1.7 mM EDTA). Protein inhibitors PMSF and Pepstatin A were added to the slurry at a final concentration of 2 mM and 1.7 μM respectively. Cells were lysed by 3–5 passages in a microfluidizer. The lysates were clarified by centrifugation at 5000×g for 10 min. The supernatant was layered on top of a 5 cm cushion of 45% (v/v) sucrose in L1 buffer and the L1, L2 or L1 and L2 proteins were pelleted by centrifugation at 100,000×g for 4 hours. The pellet was resuspended in ¹⁄₁₀th the volume of L1 buffer. The resuspended pellet was clarified by centrifugation at 5000×g for 10 min.

For EM analysis (Structure Probe, West Chester, Pa.), an aliquot of each sample was placed on 200 mesh carbon coated copper grids. A drop of 2% phosphotungstic acid (PTA), pH 7.0 was placed on the grid for 20 seconds. The grids were allowed to air dry prior to TEM examination. All microscopy was done using a JEOL L100CX transmission electron microscope (JEOL USA, Inc.) at an accelerating voltage of 100 KV. The micrographs generated have a final magnification of 100,000X.

Figure 7:
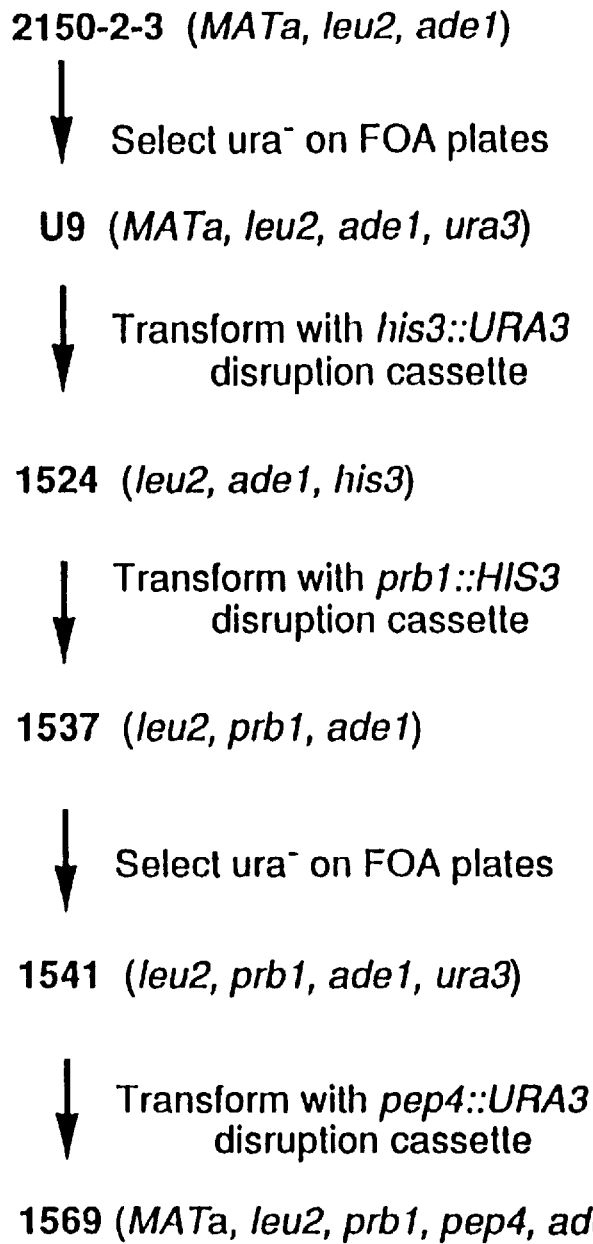
FIG. 7 is a schematic overview of the construction of S. cerevisiae strain 1558.
Figure 8:
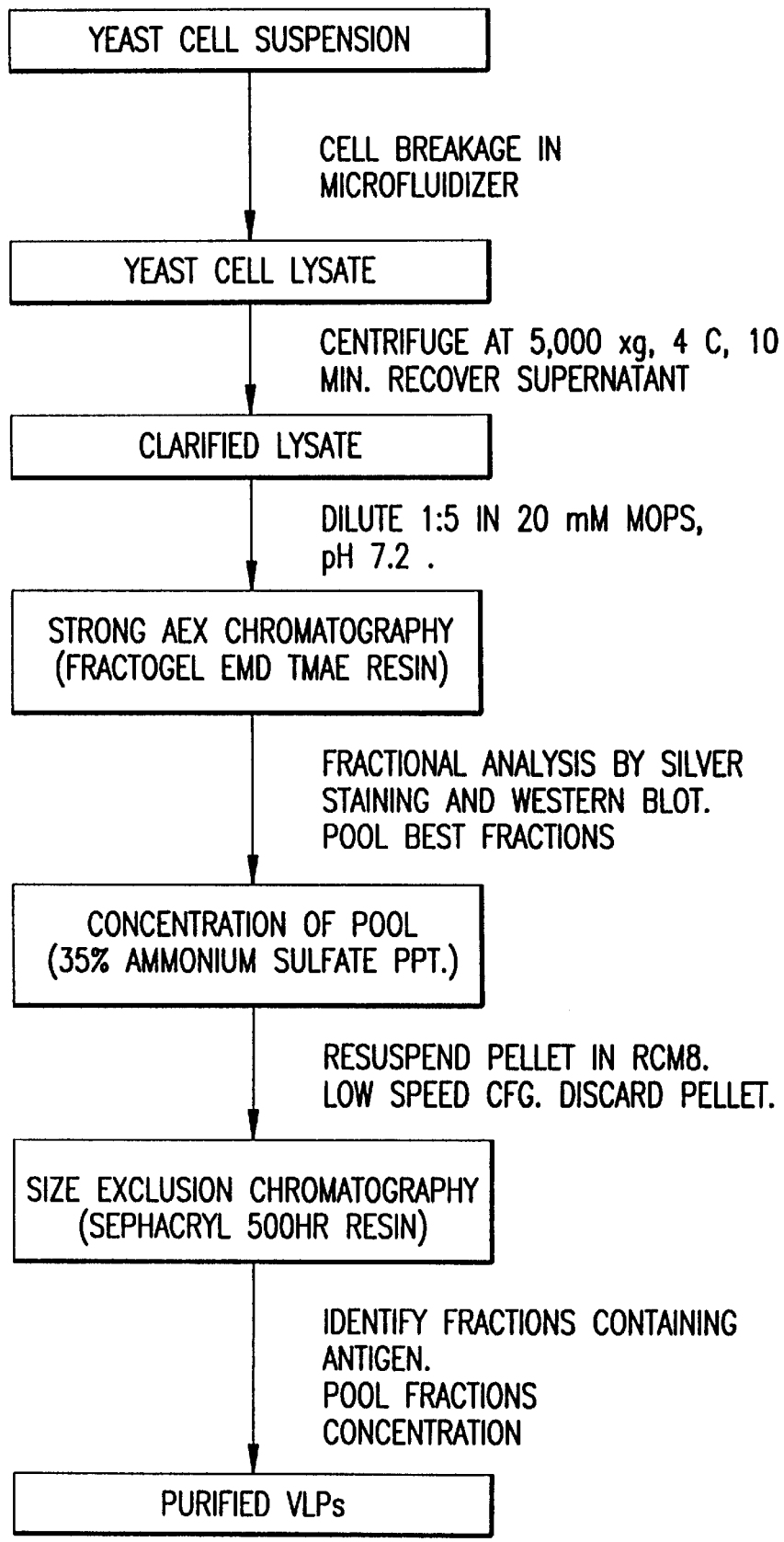
FIG. 8 is a schematic overview of the construction of S. cerevisiae strain 1569.
Figure 10A:
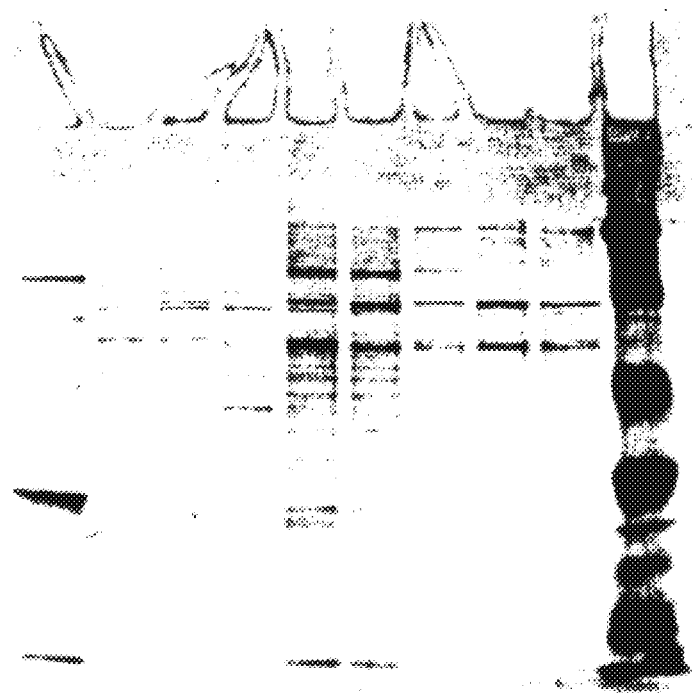
FIG. 10 is list of strains.
Figure 10B:
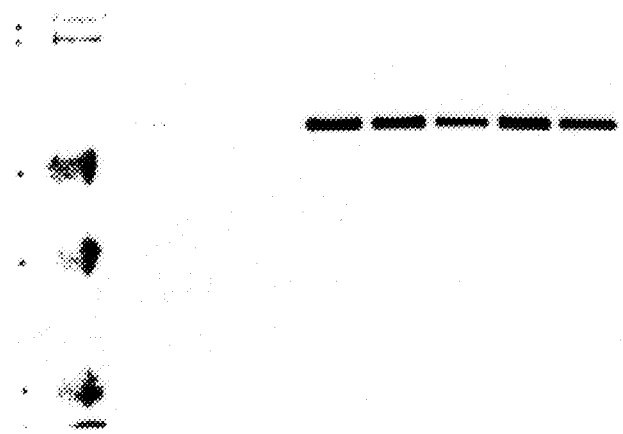
Figure 10C:
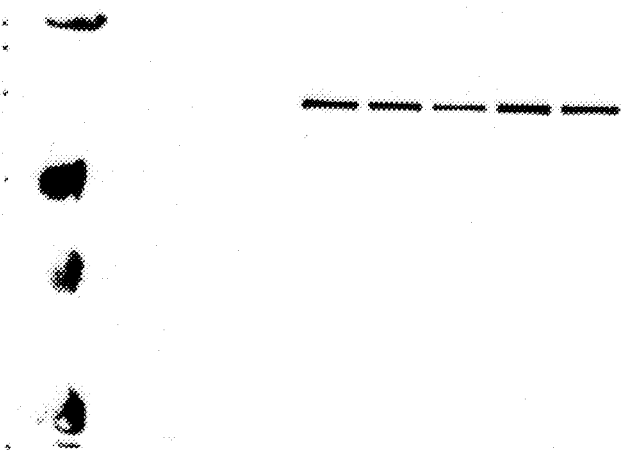
Figure 11:
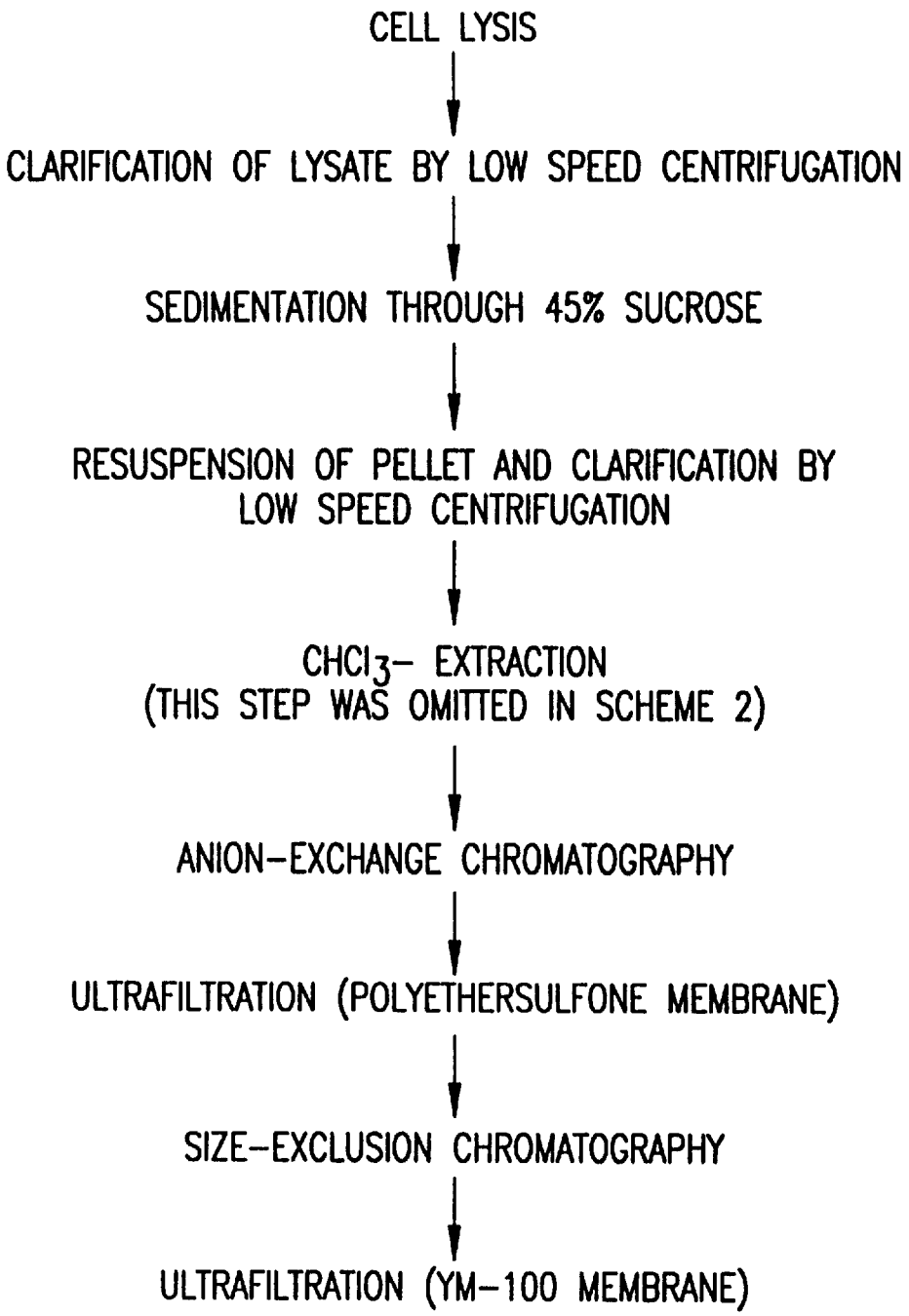
FIG. 11 shows a set of SDS-PAGE analyses of HPV16 L1+L2 purified from yeast. In addition to the final purified VLP, retains from intermediate steps in the purification process are included. The table provides identification of the sample in each lane. A gel stained with colloidal Coomassie as well as Western blots probed with antisera to L1 and L2 proteins are included.
Figure 12:
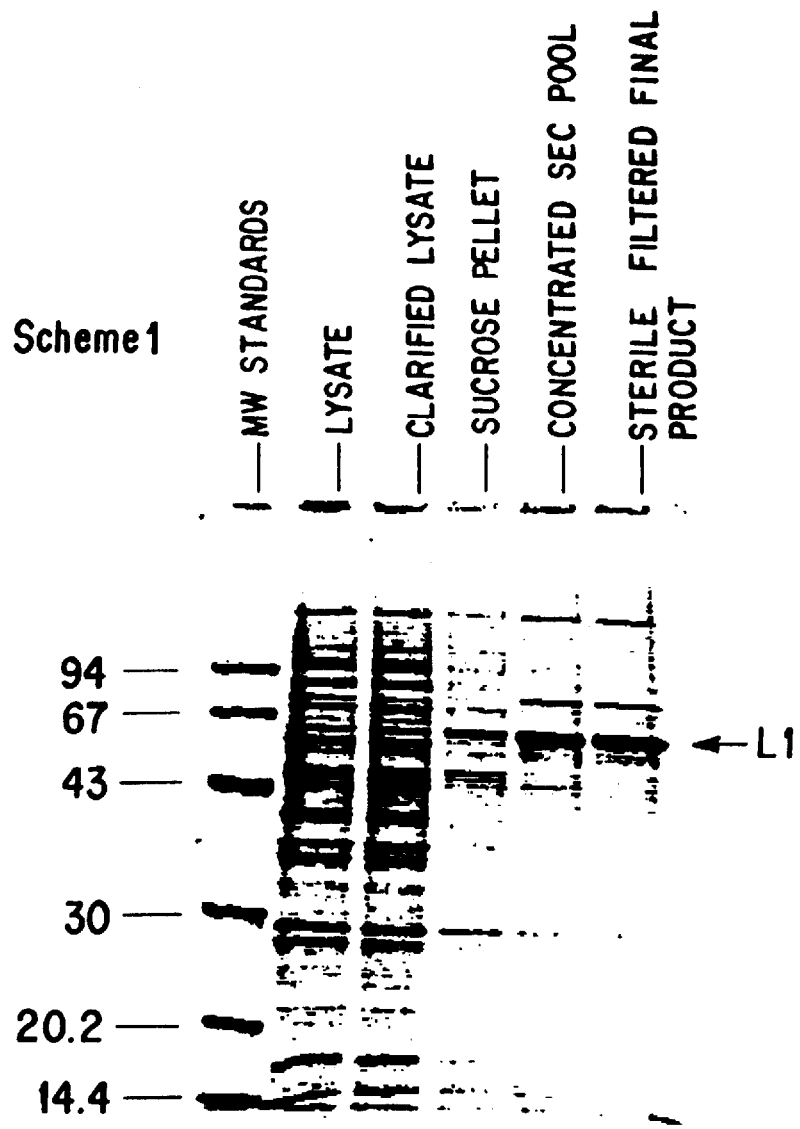
FIG. 12 is a schematic of alternative cottontail rabbit papillomavirus L1 purification processes.
Figure 14:
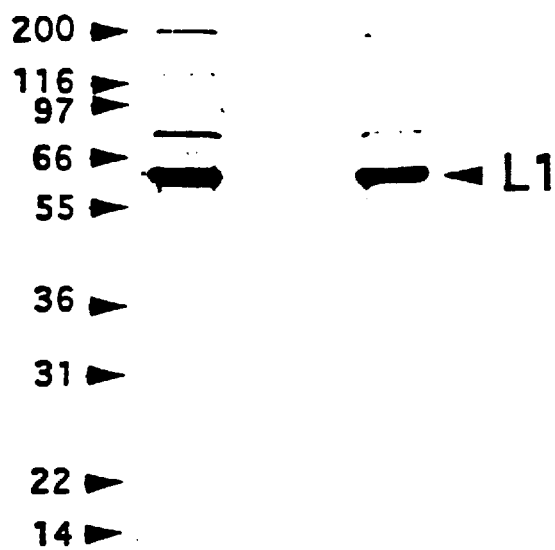

In all yeast samples harboring either the CRPV L1 expression plasmid or plasmids for the co-expression of CRPV L1 and L2, VLP were observed in the 50–55 nm diameter size range. No VLP were observed in yeast control samples or yeast samples harboring the L2 expression plasmid alone. (FIGS. 7, 8, 9).

EXAMPLE 20

Purification of Recombinant CRPV L1 Capsid Protein—Scheme 2

All steps were performed at 4° C. unless specified.

Cells stored at −70° C. were thawed and suspended in an equal volume of Breaking buffer (20 mM sodium phosphate, pH 7.2, 100 mM NaCl, 1.7 mM EDTA). Protease inhibitors PMSF and Pepstatin A were added to the slurry to final concentrations of 2 mM and 1.7 μM respectively. Cells were lysed using a BioNeb Cell Disruptor system (Glas-Col Apparatus Co., Terra Haute, Ind.). The lysate was clarified by centrifugation at 5000×g for 10 minutes.

The supernatant was layered on top of a 5 cm cushion of 45% sucrose (w/v) in L1 buffer, and L1 was pelleted by centrifugation at 100,000 ×g for 4 hours. The pellet was resuspended in ¹⁄₁₀ volume of L1 buffer. The resuspended pellet was clarified by centrifugation at 5000×g for 10 minutes.

Supernatant was diluted 1:5 with PBS, reclarified by centrifugation in Sorvall SA-600 rotor at 6500 rpm for 10 minutes at 4° C. The supernatant was filtered through a 0.22 micron syringe filter and fractionated by anion-exchange chromatography.

Anion-exchange chromatography was performed with a Perkin-Elmer Series 410 Biopump HPLC with a 5 milliliter injection loop. The chromatography medium was a Fractogel EMF TMAE-650 (S) 25–40 micron resin (EM Separations, Gibbstown, N.J.) in a 150 mm×10 mm ID glass column. To monitor elution of protein from the column, optical detection at 280 nm was accomplished with a Perkin-Elmer LC-235 diode array detector. The column was pre-equilibrated with 0.15M NaCl in 0.01M sodium phosphate buffer, pH 7.2 (Buffer A). The column was run at a flow rate of 0.75 ml/min. The sample was loaded on the column, and the column was washed with Buffer A to remove unbound material. Bound material was eluted with a linear concentration gradient of sodium chloride, 0.15M to 0.65M for 5 minutes, followed by a 0.65M to 1.15M linear gradient for 30 minutes. Detection of antigen in fractions collected during elution was accomplished by immuno dot blot assay. Fractions containing immunoreactive material (i.e., fractions eluting between 0.81M and 1.05M NaCl) were pooled.

The pooled fractions were concentrated in Macrosep centrifugal concentration devices (Filtron Technology Corp., Northborough, Mass.) to ⅕ volume.

The concentrate was fractionated by size-exclusion chromatography using Sephacryl S-1000 SF resin (Pharmacia, Piscataway, N.J.) in a 87×27 mm ID column. The column was run at a flow rate of 2.5 ml/min. Elution of protein was monitored by absorbance at 280nm. Antigen was detected by immunoblot.

Fractions containing immunoreactive material were pooled and concentrated by ultrafiltration using a stirred cell (Amicon, Inc., Beverly, Mass.) with a 43 mm diameter YM-100 flat sheet membrane (Amicon, Inc., Beverly, Mass.) under nitrogen at 10 psi pressure.

The final product was characterized by SDS/PAGE with Coomassie staining, and by solution-sieving capillary electrophoresis (SSCE). The final product from Scheme 2 was 88% pure by SSCE.

EXAMPLE 21

A. Purification of Recombinant CRPV L1 Capsid Protein - Scheme 3

All steps were performed at 4° C. unless specified.

Cells stored at −70° C. were thawed and suspended in an equal volume of Breaking buffer (20 mM sodium phosphate, pH 7.2, 100 mM NaCl, 1.7 mM EDTA). Protease inhibitors PMSF and Pepstatin A were added to the slurry to final concentrations of 2 mM and 1.7 μM respectively. Cells were lysed using a BioNeb Cel L1 1 Disruptor system (Glas-Col Apparatus Co., Terra Haute, Ind.). The lysate was clarified by centrifugation at 5000×g for 10 minutes.

The supernatant was layered on top of a 5 cm cushion of 45% sucrose (w/v) in L1 I buffer, and L1 was pelleted by centrifugation at 100,000×g for 4 hours. The pellet was resuspended in ⅒th volume of buffer. The resuspended pellet was clarified by centrifugation at 5000×g for 10 minutes.

The supernatant was extracted with ½ volume of chloroform. The aqueous layer was removed and clarified by centrifugation at 12,000 rpm in a Beckman microfuge for 5 minutes at room temperature.

Supernatant was diluted 1:5 with PBS, reclarified by centrifugation in Sorvall SA-600 rotor at 6500 rpm for 10 minutes at 4° C. The supernatant was filtered through a 0.22 micron syringe filter and fractionated by anion-exchange chromatography.

Anion-exchange chromatography was performed with a Perkin-Elmer Series 410 Biopump HPLC with a 5 milliliter injection loop. The chromatography medium was a Fractogel EMF TMAE-650 (S) 25–40 micron resin (EM Separations, Gibbstown, N.J.) in a 150mm×10 mm ID glass column. To monitor elution of protein from the column, optical detection at 280 nm was accomplished with a Perkin-Elmer LC-235 diode array detector. The column was pre-equilibrated with 0.15M NaCl in 0.01M sodium phosphate buffer, pH 7.2 (Buffer A). The column was run at a flow rate of 0.75 ml/min. The sample was loaded on the column, and the column was washed with Buffer A to remove unbound material. Bound material was eluted with a linear concentration gradient of sodium chloride, 0.15M to 0.65M for 5 minutes, followed by a 0.65M to 1.15M linear gradient for 30 minutes. Detection of antigen in fractions collected during elution was accomplished by immuno dot blot assay. Fractions containing immunoreactive material (i.e., fractions eluting between 0.81M and 1.05M NaCl) were pooled.

The pooled fractions were concentrated in Macrosep centrifugal concentration devices (Filtron Technology Corp., Northborough, Mass.) to ⅕ volume.

The concentrate was fractionated by size-exclusion chromatography using Sephacryl S- 1000 SF resin (Pharmacia, Piscataway, N.J.) in a 87 cm×27 mm ID column. The column was run at a flow rate of 2.5 ml/min. Elution of protein was monitored by A280 nm. Antigen was detected by immunoblot.

Fractions containing immunoreactive material were pooled and concentrated by ultrafiltration using a stirred cell (Amicon, Inc., Beverly, Mass.) with a 43 mm diameter YM-100 flat sheet membrane (Amicon, Inc., Beverly, Mass.) under nitrogen at 10 psi pressure.

The final product was characterized by SDS/PAGE with Coomassie staining, and by solution-sieving capillary electrophoresis (SSCE). The final product from Scheme 3 was 95% pure by SSCE.

EXAMPLE 22

Expression of CRPV L1 and HPV Type 6a L1 (strain 1644) in enriched complex and chemically-defined media Inocula for these strains were developed in leucine-free synthetic medium as described above for transfer to shake flask cultures. The shake flasks used were baffled for high aeration capacity (70 mL liquid per 300 mL flask, Tunair Labware) and media were supplemented with ca. 0.5 L1 rn L1 mL/L of an antifoam (UCON LB-625, Union Carbide). Enriched complex medium contained (per L): 40 g Difco yeast extract; 20 g Sheffield HySoy peptone; 30 g glucose; 50 g galactose; the medium was adjusted to pH 5.3 prior to sterilization. The chemically-defined medium used was similar to that described by Oura (Biotechnol. Bioengineer.16:1197–1212. 1974) but supplemented with (per L): 0.1 g choline Cl; 0.4 g adenine; 30 g monosodium glutamate as nitrogen source; 0.2 g uracil; 20 g glucose; 40 g galactose. Flasks were inoculated with 3 mL inoculum and incubated for 66 hr at 28° C., 250 rpm on a rotary shaker. Flasks were sampled at intervals for verification of expression by immunoblot using anti-CRPV L1 and anti-HPV 6a L1 antisera.

EXAMPLE 23

Cloning of HPV-6a Genome

Tissue from a patient diagnosed with severe condylomata acuminata (provided by Dr. Darron Brown, Indiana University School of Medicine) was typed by restriction enzyme digestion and polymerase chain reaction (PCR) and was shown to contain HPV type 6a. DNA was extracted from the tissue sample and digested with HindIII enzyme. Following size-fractionation through a 0.8% low melting temperature agarose prep gel, the 8-kb region was excised from the gel and the agarose was digested with Gelase™ enzyme (Epicentre Technologies, Inc.). The sample was ligated with pUC18 which had been digested with HindIII and dephosphorylated (Pharmacia, Inc). Following transformation of competent E. coli DH5 cells (BRL), the plasmid library was screened for HPV-6a positive clones using a $^{32}$P-labeled oligodeoxynucleotide that was complementary to the HPV-6a L1 gene. A pUC18 plasmid containing the 8-kb HPV-6a genome was isolated and characterized by restriction enzyme and Southern blot analyses. This plasmid was designated, pUC1 8-HPV-6a. The complete 8-kb HPV-6a genome was sequenced using the ABI automated sequencer (#373A) according to the manufacturer's instructions.

A large vulvar condyloma acuminatum lesion was obtained from a 25 year old, postpartum female patient. A fragment of the lesion was frozen in liquid nitrogen, then processed with a Braun mikro-dismembrator II (B. Braun Instruments, Melsungen, Germany). The resulting material was solubilized with 0.6% (w/v) sodium dodecyl sulfate (SDS), treated with proteinase K (50 mcg/ml), and extracted with phenol/chloroformlisoamyl alcohol. DNA was ethanol-precipitated and quantified by UV spectrophotometry. The presence of high-molecular-weight DNA was established by agarose gel electrophoresis followed by staining with ethidium bromide.

The HPV DNA type was determined using the hybrid capture assay marketed as ViraType Plus (Digene Diagnostics, Beltsville, Md.). The HPV probes used were divided into two pools whose composition is based on the association of each type with genital tract malignancies. Probe group A contained the "low-risk" types HPV6, 11, 42, 43, and 44 while probe B contained the "high-risk" types 16, 18, 31, 33, 35, 45, 51, 52, and 56. Total DNA was digested with PstI, BamHI, and HindIII and Southern blots were performed under high stringency conditions (Tm-15° C.) to determine the HPV subtype.

To determine the complete HPV6a sequence, sequencing primers were synthesized based on the published HPV6b sequence. Both strands of the complete 8.1-kbp HPV6a genome were sequenced by the dideoxy chain termination method using the PRISM™ kit and an Applied Biosystems (ABI) automated sequencer (#373A) according to the manufacturers' instructions (ABI, Inc., Foster City, Calif.). In cases where the sense and antisense sequence did not match, additional HPV6a specific primers were synthesized to resequence in both directions over the area in question to obtain a consensus.

The DNA sequences of HPV6a and HPV6b exhibited over 97% identity with a total of 229 bp changes identified out of 8010 bp. The most significant differences compared to the HPV6b sequence were found in the long control region (LCR; nt 7205-nt 106). Apart from several single nucleotide (nt) changes in the HPV6a LCR, a 94-bp insertion at nt 7350 and another 19-bp insertion at nt 7804 were found. At nt 7615, six base pairs were deleted from the HPV6a genome.

EXAMPLE 24

Construction of HPV6a L1 Yeast Expression Vector

HPV type 6a DNA was used as a template for PCR. The HPV6a L1 i gene was amplified by PCR using Vent L1-polymerase (New England Biolabs, Inc.), 35 cycles of amplification (94° C. 1 min, 48° C. 1 min, 72° C. 1 min 45 sec), and the following oligodeoxynucleotide primers which contain flanking Bgl II sites (underlined):

sense primer: 5'-CTC AGA TCT CAC AAA ACA AAA TGT GGC GGC CTA GCG ACA GCA CAG-3'(SEQ ID NO:11)

antisense primer: 5'-GAG AGA TCT TAC CTT TTA GTT TTG GCG CGC TTA C-3'(SEQ ID NO:12)

The sense primer introduces a yeast non-translated leader sequence immediately upstream to the HPV6a L1 initiating methionine codon (highlighted in bold print). The 1.5-kbP L1 PCR product was digested with BglII and gel-purified. The pC1/1-GAL expression vector was constructed by isolating the 1.4 kbp SphI fragment from the bidirectional promoter vector pUC L1 I8-GAL1p-GAL10p which contains the divergent GAL1/GAL10 promoter from the plasmid pBM272 (provided by Dr. Mark Johnston, Washington University, St. Louis) flanked on each side by a copy of the yeast ADH L1 J transcriptional terminator [Bennetzen, J. L. and Hall, B. D. (1982) *J. Biol. Chem.* 257:3018–3025]. In the resulting expression cassette, a BamHI site is located between the GAL1 promoter and the first copy of the ADH1 transcriptional terminator and a SmaI cloning site is located between the divergent GAL10 promoter and the second copy of the ADH L1 transcriptional terminator. The yeast shuttle vector pC1/1 (Rosenberg et al., *Nature* 312 (1984) 77–80) was digested with SphI and ligated with the 1.4-kbp Sph L1 1 GAL promoter fragment. The resulting vector, pC1/1-GAL, was linearized with BamHI which cuts between the GAL1 promoter and the ADH1 transcription terminator. The BamHI digested pC1/1-GAL vector and the BglL digested HPV6a L1 PCR fragment were ligated and used to transform *E. coli* DH5 cells (BRL). A pC1/1-GAL plasmid was isolated which contains the HPV-6a L1 gene and was designated p13173-357-6. The L1 gene in p13173–357–6 was sequenced (ABI Sequencer #373A) and shown to be identical to the L1 gene in the pUC18-HPV6a clone.

EXAMPLE 25

Construction of the HPV6a L1 and L2 Yeast Expression Vector

Plasmid p13173-357-6 (pC1/1-GAL+HPV6a L1) was digested with SmaI, which cuts between the GAL10 promoter and the ADH1 transcription terminator. The 1.4-kbp HPV6a L2 gene was amplified by PCR using the pUC18-HPV6a DNA as template, Vent polymerase (New England Biolabs, Inc.), 10 cycles of PCR amplification (94° C., 1 min; 48° C., 1 min; 72L1 ° C, 1 min 45 sec) and the following oligodeoxynucleotide primers which contain flanking SmaI sites (underlined):

sense primer: 5'-TCC CCC GGG CAC AAA ACA AAA TGG CAC ATA GTA GGG CCC GAC GAC-3'(SEQ ID NO: 13)

antisense primer: 5'-TCC CCC GGG CTA GGC CGC CAC ATC TGA AAA AAA TAA GG-3'(SEQ ID NO:14)

The sense primer introduces a yeast non-translated leader sequence immediately upstream to the HPV6a L2 initiating methionine codon (highlighted in bold print). The PCR fragment was digested with SmaI, gel purified and ligated with the SmaI digested p13173-357-6 plasmid. A pC1/1-GAL plasmid containing both the HPV6a L1 and L2 genes was isolated and designated, p14049-7-2. The L2 gene was sequenced (ABI Sequencer #373A) and found to be identical to the L2 gene in the pUC18-HPV6a clone.

EXAMPLE 26

Expression of HPV6a L1 and Co-Expression of HPV6a L1 and L2 in Yeast

Plasmids p13173-357-6 (pC1/1-GAL+HPV6a L1) and p14049-7-2 (pC1/1 -GAL+HPV6a L1 and L2) were used to transform *S. cerevisiae* strains #1569 (MATa, leu2-04, prbl, adel, pep4, cir°) and #1558 (MATa, leu2-04, prbl, mnn9, adel, cir°). The resulting recombinant strains obtained using host strain #1558 were strains #1644 (HPV6a L1 ) and #1670 (HPV6a L1+L2) as shown in the table. Clonal isolates were grown at 30° C. in YEHD medium containing 2% galactose for 68–78 hours. After harvesting the cells, the cell pellets were broken with glass beads and cell lysates analyzed for the expression of HPV6a L1 or HPV6a L2 protein by immunoblot analysis. Samples containing 40 μg of total cellular protein were electrophoresed on 10% Tris-Glycine gels under reducing and denaturing conditions and electroblotted onto nitrocellulose filters. The L1 protein was immunodetected using rabbit antisera raised against a trpE-HPV1 L1 I fusion protein (Brown, D. R. et al., *Virology* 201:46–54) as primary antibody and donkey anti-rabbit IgG horseradish peroxidase-linked (HRP) whole antibody (Amersham, Inc.) as the secondary antibody. The filters were processed using the chemiluminescent ECL1 w Detection Kit (Amersham, Inc.). A 50–55 kDa L1 protein band was detected in all samples except the negative control (pC1/1 without L1 or L2 gene).

The L2 protein was detected as a 70 kDa protein band by Western analysis using 1:250 diluted sera from mice which had been immunized 3 times with a trpE-HPV6a L2 fusion protein prepared essentially according to the method of Carter et al. as the primary antibody and HRP-linked, sheep anti-mouse IgG (Amersham, Inc.) as a second antibody (1:1000 dilution).

For EM analysis (Structure Probe, West Chester, Pa.), an aliquot of each sample was placed on 200 mesh carbon coated copper grids. A drop of 2% phosphotungstic acid (PTA), pH 7.0 was placed on the grid for 20 seconds. The grids were allowed to air dry prior to TEM examination. All microscopy was done using a JEOL 100CX transmission electron microscope (JEOL USA, Inc.) at an accelerating voltage of 100 KV. The micrographs generated have a final magnification of 100,000X.

VLP were observed in the 50–55 L1 mn diameter size range in all yeast samples harboring either the HPV6a L1 or HPV6a L1 and L2 coexpression plasmids. No VLP were observed in yeast control samples.

EXAMPLE 27

Fermentation of HPV6a L1+L2 (Strain #1670)

Surface growth of a plate culture of strain 1670 was aseptically transferred to a leucine-free liquid medium containing (per L): 8.5 g Difco yeast nitrogen base without amino acids and ammonium sulfate; 0.2 g adenine; 0.2 g uracil; 10 g succinic acid; 5 g ammonium sulfate; and 0.25 g L tyrosine; this medium was adjusted to pH 5.0–5.3 with NaOH prior to sterilization. After growth for 25 hr at 28° C., 250 rpm on a rotary shaker, frozen culture vials were prepared by adding sterile glycerol to a final concentration of 17% (w/v) prior to storage at −70° C. (1 mL per cryovial). Inoculum for fermentation of strain 1670 was developed in the same medium (500 mL per 2-L flask) and was started by transferring the thawed contents of two frozen culture vials to the 2-L flasks and incubating at 28° C., 250 rpm on a rotary shaker for 25 hr. Fermentation of strain 1670 used a New Brunswick SF- 1 16 fermentor with a working volume of 10 L after inoculation. The production medium used contained (per L): 20 g Difco yeast extract; 10 g Sheffield HySoy peptone; 20 g glucose; 20 g galactose; the medium was adjusted to pH 5.3 prior to sterilization. The entire contents (500 mL) of the 2-L inoculum flask was transferred to the fermentor which was incubated at 28° C., 5 L air per min, 400 rpm, 3.5 psi pressure. Agitation was increased as needed to maintain dissolved oxygen levels of greater than 40% of saturation. Progress of the fermentation was monitored by offline glucose measurements (Beckman Glucose 2 Analyzer) and online mass spectrometry (Perkin-Elmer 1200). After 69 hr incubation, a cell density of 9.9 g dry cell weight per L was reached. The culture was concentrated by hollow fiber filtration (Amicon H5MP01-43 cartridge in an Amicon DC- L10 filtration system) to ca. 2 L, diafiltered with 2 L phosphate-buffered saline, and concentrated further (to ca. 1 L) before dispensing into 500 mL centrifuge bottles. Cell pellets were collected by centrifugation at 8,000 rpm (Sorval GS3 rotor) for 20 min at 4° C. After decanting the supernatant, the pellets (total 225 g wet cells) were stored at −70° C. until use.

EXAMPLE 28

Purification of Recombinant HPV6a L1+L2 Capsid Proteins

All steps performed at 4° C. unless noted.

Cells of strain #1670 were stored frozen at −70 ° C. Frozen cells (wet weight=38.0 g) were thawed at 20°–23° C. and resuspended in 50 mL "L1 Buffer" (20 mM sodium phosphate, pH 7.2, 100 mM NaCl, 1.7 mM EDTA). The protease inhibitors PMSF and pepstatin A were added to final concentrations of 2 mM and 1.7 µM, respectively. The cell slury was broken at a pressure of approximately 8,000 psi by 3 passes in a M110 Microfluidizer (Microfluidics Corp., Newton, Mass.). The broken cell slurry was centrifuged at 5,000×for 10 min to remove cellular debris. The supernatant liquid containing L1+L2 antigen was recovered.

The supernatant liquid was diluted 1:5 by addition of Buffer A (20 mM MOPS, pH 7.0) and applied to an anion exchange capture column (5.0 cm ID×4.0 cm) of Fractogel® EMD TMAE-650 (S) resin (EM Separations, Gibbstown, N.J.) equilibrated in Buffer A. Following a wash with Buffer A, the antigen was eluted with a gradient of 0–1.0M NaCl in Buffer A. Immuno-dot blotting was performed to determine which fractions from the column contained L1 protein.

Fractions containing L1 protein as determined by immunodot blot were assayed for total protein by the Bradford method followed by SDS-PAGE using silver staining and Western blotting.

TMAE fractions showing comparable purity and enrichment of L1 protein were pooled. The antigen was concentrated by ammonium sulfate fractionation. The solution was adjusted to 63% saturated ammonium sulfate by adding solid reagent while gently stirring over 30 min. The sample was placed on ice and precipitation allowed to proceed for 30 min. The sample was centrifuged at 12,000×g. The pellet was resuspended in 20.0 mL PBS (6.25 mM Na phosphate, pH 7.2, 150 mM NaCl).

The resuspended pellet was chromatographed on a size exclusion column (2.6 cm ID×89 cm) of Sephacryl 500 HR resin (Pharmacia, Piscataway, N.J.). Running buffer was PBS. Chromatography performed at 20°–23° C. Fractions were analyzed by SDS-PAGE using silver staining and western blot detection. The purest fractions were pooled. The resulting pool was concentrated.

Final product was analyzed by SDS-PAGE using colloidal Coomassie staining. The L1 and L2 proteins were estimated to be 85% homogeneous. The identity of L1 and L2 proteins was confirmed by western blotting using the appropriate antisera. The final product was aliquoted and stored at −70° C. This process resulted in a total of 3.0 mg protein.

Electron microscopy analysis was performed by Structure Probe (West Chester, Pa.). An aliquot of sample was placed on a 200 mesh carbon-coated copper grid. A drop of 2% phosphotungstic acid, pH 7.0 was placed on the grid for 20 seconds. The grid was allowed to air dry prior to TEM examination. All microscopy was performed using a JEOL 100 CX transmission electron microscope (JEOL USA, Inc.) at an accelerating voltage of 100 kV. The micrographs generated have a final magnification of 100,000×. The presence of virus-like particles in the 50–55 nm size range was confirmed.

EXAMPLE 29

Purification of HPV-6a L1 and L1/L2 VLPs for EM Studies

The yeast-expressed HPV-6a L1 and HPV-6a L1+L2 proteins were partially purified and concentrated for electron microscopy (EM) studies. One to 1.5 liters of YEHD medium containing 2% galactose and 0.1M sorbitol were inoculated with S. cerevisiae strain #1558 harboring either plasmid p13173-357-6 (L1 expression vector) or plasmid p14049-7-2 (L1 and L2 co-expression vector) and grown at 30° C. for 68–78 hours. The cells were harvested by centrifugation at 4,000 g for 10 min, and cell pellets were frozen at −70° C. All following steps were performed at 4° C. Cell pellets were thawed and suspended in an equal volume of "L1 buffer" (20 mM sodium phosphate, pH 7.2, 100 mM NaCl, 1.7 mM EDTA). Protease inhibitors PMSF and Pepstatin A were added to the slurry to final concentrations of 2 mM and 1.7 µM respectively. Cells were lysed by 3–5 passes in a microfluidizer. The lysate was clarified by centrifugation at 5000×g for 10 minutes. The supernatant was layered on top of a 5 cm cushion of 45% (w L1 /v) sucrose in L1 buffer, and the L1 or L1+L2 proteins were pelleted by centrifugation at 100,000×g for 4 hours. The pellet was resuspended in 1/10th volume of L1 buffer and clarified by centrifugation at 5000×g for 10 minutes. Samples were studied by EM and shown to contain virus-like particles.

EXAMPLE 30

Cloning of HPV16 L1 and L2 Genes

Total genomic DNA was extracted from Caski cells (ATCC #CRL 1550) by standard techniques (Sambrook et al., supra). The DNA was digested with Bst 1107I and SphI endonucleases and electrophoresed through a 0.8% low-melting-temperature agarose preparative gel. A region corresponding to DNA of _3.5-kbp was excised from the gel and the agarose was digested with Gelase™ enzyme (Epicentre Technologies, Inc.). The gel-purified DNA was made blunt-ended with T4 DNA polymerase and ligated with blunt-ended, phosphorylated oligodeoxynucleotide linkers that contain a buried HindIII site. The ligation mixture was digested to completion with HindIII and the _3.5-kbp DNA was size-fractionated through an agarose gel as described above. The gel-purified DNA was ligated with pUC18 plasmid DNA that had been digested with HindIII and dephosphorylated. Following transformation of competent E. coli DH5 cells (BRL), the plasmid library was screened for HPV 16-positive clones by colony hybridization using an antisense $^{32}$P-labeled oligodeoxynucleotide that is complementary to the 3'-end of the HPV-16 L1 gene (5'-GAG AGA TCT TAC AGC TTA CGT TTT TTG CGT TTA GC-3'). A pUC18 plasmid containing a 3.3-kbp HPV 16 genomic fragment was isolated and characterized by restriction enzyme and Southern blot analyses. This plasmid was designated pUC18-HPV16 L1/L2 and contains all of the L1 and L2 coding DNA sequences. Plasmid DNA was prepared using the Qiagen™ Plasmid Maxi kit (Qiagen, Inc.).

EXAMPLE 31

Construction of HPV 16 L1 Yeast Expression Vector

The clone, pUC18-HPV16 L1/L2 was used as a template for PCR. The HPV16 L1 gene was amplified by PCR using Vent polymerase (New England Biolabs, Inc.), 10 cycles of amplification (94° C., 1 min; 48° C., 1 min; 72° C., 1 min 45 sec), and the following oligodeoxynucleotide primers which contain flanking BglII sites (underlined):

sense primer: 5'-CTC AGA TCT CAC AAA ACA AAA TGT CTC TTT GGC TGC CTA TGT AGG CC-3'(SEQ ID NO:15)

antisense primer: 5'-GAG AGA TCT TAC AGC TTA CGT TTT TTG CGT TTA GC-3'(SEQ ID NO:16)

The sense primer introduces a yeast non-translated leader sequence immediately upstream to the HPV16 L1 initiating methionine codon (highlighted in bold print). The 1.5-kbp L1 PCR product was digested with Bgl L1 .U, gel-purified, and ligated with the BamHI digested pC1/1-GAL vector. A pC1/1-GAL plasmid was isolated containing the HPV16 L1 gene and designated, p14049-37-1. The L1 gene in p14049-37-1 was sequenced using the PRISM™ kit (ABI, Inc.) and an ABI Sequencer Model #373A according to the manufacturer's directions. The L1 gene in this isolate was shown to contain 3 nucleotide changes from the corrected, published prototype sequence (Kimbauer, R. et al. (1993) J. Virol. 67: 6929–6936), resulting in two amino acid changes: His-202 to Asp; Thr-266 to Ala. Sequence analysis of the original template DNA confirmed that these changes were also present in the genomic clone pUC18-HPV16 L1/L2 and were not introduced by the PCR.

EXAMPLE 32

Construction of the HPV16 L1 and L2 Yeast Expression Vector

Plasmid p14049-37-1 (pC1/1-GAL+HPV16 L1) was digested with SmaI, which cuts between the GAL10 promoter and the ADH1 transcription terminator. The 1.4-kbp HPV 16 L2 gene was amplified by PCR using the pUC18-HPV16 L1/L2 DNA as template, Vent polymerase (New England Biolabs, Inc.), 10 cycles of PCR amplification (94° C., 1 min; 48° C., 1 min; 72° C., 1 min 45 sec) and the following oligodeoxynucleotide primers which contain flanking SmaI sites (underlined):

sense primer: 5'-TCC CCC GGG CAC AAA ACA AAA TGC GAC ACA AAC GTT CTG CAA AAC-3'(SEQ ID NO:17)

antisense primer: 5'-TCC CCC GGG CTA GGC AGC CAA AGA GAC ATC TGA-3'(SEQ ID NO: 18)

The sense primer introduces a yeast non-translated leader sequence immediately upstream to the HPV 16 L2 initiating methionine codon (highlighted in bold print). The 1.4-kbp L2 PCR product was digested with Smal, gel-purified, and ligated with the Smal digested p14049–37–1 vector. A pC1/1-GAL plasmid containing both the HPV16 L1 and L2 genes was isolated and designated, p14049–42–2. The L2 gene in p14049-42-2 was sequenced using the PRISM™ kit (ABI, Inc.) and an ABI Sequencer Model #373A according to the manufacturer's directions. The L2 gene in this isolate was shown to contain 5 nucleotide changes from the corrected, published prototype sequence (Kirnbauer, R. et al. (1993) supra), resulting in one amino acid change: Ser-269 to Pro. Sequence analysis of the genomic clone pUC18-HPV16 L1/L2 confirmed that this change was also present in the original template DNA and was not introduced by the PCR.

EXAMPLE 33

A. Expression of HPVI6 L1 and Co-Expression of HPV16 L1 and L2 in Yeast

Plasmids p14049-37-1 (pC1/1 -GAL+HPV16 L1 ) and p14049-42-2 (pC1/1-GAL+HPV16 L1 and L2) were used to transform S. cerevisiae strain #1558. The resulting recombinant strains were #1678 (HPV16-L1) and #1679 (HPVI6 L1+L2) as shown in the table. Clonal isolates were grown at 300C in YEHD medium containing 2% galactose for 68–78 hours. After harvesting the cells, the cell pellets were broken with glass beads and cell lysates analyzed for the expression of HPV16 L1 or HPV1 6 L2 protein by immunoblot analysis. Samples containing 40 mcg of total cellular protein were electrophoresed on 10% Tris-Glycine gels under reducing and denaturing conditions and electroblotted onto nitrocellulose filters. The HPV16 L1 protein was immunodetected using rabbit polyclonal antisera raised against a trpE-HPVL1 I L1 I L1 fusion protein (D. Brown et al., Virology 201:46–54) as primary antibody and HRP-linked, donkey anti-rabbit IgG antibody (Amersham, Inc.) as the secondary antibody. The filters were processed using the chernilumi-nescent ECL Detection kit (Amersham, Inc.). A 50–55 kDa L1 protein band was detected in all samples except the negative control (pC1/1 without L1 or L2 gene). The L2 protein was detected as a 70 kDa) protein band by immunoblot using mouse anti-HPV16 L2 sera raised against trpE-L2 fusion proteins expressed in E. coli as primary antibody. Goat anti-mouse IgG HRP-linked (Amersham, Inc.) was used as secondary antibody and the filters were processed as described above.

B. Purification of Recombinant HPV Type 16 L1 +L2 Capsid Proteins

All steps performed at 4° C. unless noted.

Cells were stored frozen at −70° C. Frozen cells (wet weight=27.6 g) were thawed at 20°–23° C. and resuspended in 40 mL "L1Buffer" (20 mM sodium phosphate, pH 7.2, 100 mM NaCl, 1.7 mM EDTA). The protease inhibitors PMSF and pepstatin A were added to final concentrations of 2 mM and 1.7 $\mu$M, respectively. The cell slurry was broken at a pressure of approximately 8,000 psi by 3 passes in a M110 Microfluidizer (Microfluidics Corp., Newton, Mass.). The broken cell slurry was centrifuged at 5,000×g for 10 min to remove cellular debris. The supernatant liquid containing L1+L2 antigen was recovered.

The supernatant liquid was diluted 1:5 by addition of Buffer A (20 mM MOPS, pH 7.0) and applied to an anion exchange capture column (5.0 cm ID×4.8 cm) of Fractogel® EMD TMAE-650 (S) resin (EM Separations, Gibbstown, N.J.) equilibrated in Buffer A. Following a wash with Buffer A, the antigen was eluted with a gradient of 0–1.0M NaCl in Buffer A. Immuno-dot blotting was performed to determine which fractions from the column contained L1 protein.

Fractions containing L1 protein as determined by immunodot blot were assayed for total protein by the Bradford method followed by SDS-PAGE using silver staining and Western blotting.

TMAE fractions showing comparable purity and enrichment of L1 protein were pooled. The antigen was concentrated by ammonium sulfate fractionation. Samples were adjusted to 48% saturated ammonium sulfate by addition of solid reagent while gently stirring over 30 min. The samples were placed on ice and precipitation allowed to proceed overnight. The samples were centrifuged at 12,000×g. The pellet was resuspended in 20.0 mL PBS (6.25 mM Na phosphate, pH 7.2, 150 mM NaCl).

Resuspended pellets were chromatographed separately on a size-exclusion column (2.6 cm ID×89 cm) of Sephacryl 500 HR resin (Pharmacia, Piscataway, N.J.) at 20°–23° C. Running buffer was PBS. Fractions were analyzed by SDS-PAGE using silver staining and Western blot detection. The purest fractions were pooled. Resulting pools were concentrated in a 50 mL stirred cell using 43 mm YM-100 flat-sheet membranes (Amicon, Beverly, Mass.) at a N2 pressure of 4–6 psi.

Final product was analyzed by SDS-PAGE using colloidal Coomassie staining. The L1 and L2 proteins were estimated to be 70% homogeneous. The identity of L1 and L2 proteins was confirmed by Western blotting using the appropriate antisera. The final product was aliquoted and stored at −70° C. This process resulted in a total of 0.53 mg protein.

Electron microscopy analysis was performed by Structure Probe (West Chester, Pa.). An aliquot of sample was placed on a 200 mesh carbon-coated copper grid. A drop of 2% phosphotungstic acid, pH 7.0 was placed on the grid for 20 seconds. The grid was allowed to air dry prior to TEM examination. All microscopy was performed using a JEOL 100 CX transmission electron microscope (JEOL USA, Inc.) at an accelerating voltage of 100 kV. The micrographs generated have a final magnification of 100,000×. The presence of virus-like particles in the 50–55 nm size range was confirmed.

C. Purification of Recombinant HPV Type 16L1+ L2 Capsid Proteins

All steps performed at 4° C. unless noted.

Cells were stored frozen at −70° C. Frozen cells (wet weight=92.8 g) were thawed at 20–23 L1 ° C and resuspended in 105 mL "L1 Buffer" (20 mM sodium phosphate, pH 7.2, 100 mM NaCl, 1.7 mM EDTA). The protease inhibitors PMSF and pepstatin A were added to final concentrations of 2 mM and 1.7 $\mu$M, respectively. The cell slurry was broken at a pressure of approximately 16,000 psi by 3 passes in a M110-Y Microfluidizer (Microfluidics Corp., Newton, Mass.). The broken cell slurry was centrifuged at 6,100×g for 15 min to remove cellular debris. The supernatant liquid containing L1+L2 antigen was recovered.

The supernatant liquid was diluted 1:5 by addition of Buffer A (20 mM MOPS, pH 7.0) and applied to an anion exchange capture column (5.0 cm ID×4.2 cm) of Fractogel® EMD TMAE-650 (S) resin (EM Separations, Gibbstown, N.J.) equilibrated in Buffer A. Following a wash with Buffer A, the antigen was eluted with a gradient of 0–1.0M NaCl in Buffer A. Immuno-dot blotting was performed to determine which fractions from the column contained L1 protein.

Fractions containing L1 protein as determined by immunodot blot were assayed for total protein by the Bradford method followed by SDS-PAGE using silver staining and Western blotting.

TMAE fractions showing comparable purity and enrichment of L1 protein were pooled. The antigen was concentrated by ammonium sulfate fractionation. Samples was adjusted to 35% saturated ammonium sulfate by addition of solid reagent while gently stirring over 10 min. The samples were placed on ice and precipitation allowed to proceed for 4 hours. The samples were centrifuged at 12,000×g. The pellet was resuspended in 20.0 mL PBS (6.25 mM Na phosphate, pH 7.2, 150 mM NaCl) which contained 1 mM EDTA.

Resuspended pellets were chromatographed separately on a size-exclusion column (2.6 cm ID×89 cm) of Sephacryl 500 HR resin (Pharmacia, Piscataway, N.J.). Running buffer was PBS+1 mM EDTA. Fractions were analyzed by SDS-PAGE using silver staining and western blot detection. The purest fractions were pooled. Resulting pools were concentrated in a 50 mL stirred cell using 43 mm YM-100 flat-sheet membranes (Amicon, Beverly, Mass.) at a N2 pressure of 4–6 psi.

Final product was analyzed by SDS-PAGE using colloidal Coomassie staining. The L1 and L2 proteins were estimated to be 70% homogeneous. The identity of L1 and L2L1 proteins was confirmed by Western blotting using the appropriate antisera. The final product was aliquoted and stored at −70° C. This process resulted in a total of 3.8 mg protein.

EXAMPLE 34

A. Fermentation of Strain 1679 (HPV type 16 L1+ L2)

Procedures used for preparation frozen stock cultures, inoculum development, fermentation, and cell recovery of strain 1679 were essentially as described above. After 67 hr incubation, a cell density of 4.2 g dry cell weight per L was reached and yielded a total of 93 g wet cell pellet after recovery.

B. Fermentation of Strain 1678 (HPV type 16 L1)

Procedures used for preparation frozen stock cultures, inoculum development, fermentation, and cell recovery of strain 1678 were essentially as described above. After 70.5 hr incubation, the contents of two 10 L fermentations were pooled (a cell density of 8.7 g dry cell weight per L) which yielded a total of 258 g wet cell pellet after recovery.

C. Purification of Recombinant HPV Type 16 L1 Capsid Proteins

All steps performed at 4° C. unless noted.

Cells of strain #1678 were stored frozen at −70° C. Frozen cells (wet weight=128 g) were thawed at 20°–23° C. and resuspended in 140 mL "Modified L1 Buffer" (20 mM sodium phosphate, pH 7.2, 100 mM NaCl). The protease inhibitors PMSF and pepstatin A were added to final concentrations of 2 mM and 1.7 μM, respectively. The cell slurry was broken at a pressure- of approximately 16,000 psi by 3 passes in a M110-Y Microfluidizer (Microfluidics Corp., Newton, Mass.). The broken ell slurry was centrifuged at 11,000×g for 40 min to remove cellular debris. The supernatant liquid containing L1 antigen was recovered.

The supernatant liquid was diluted 1:5 by addition of Buffer A (20 mM MOPS, pH 7.0) and applied to an anion exchange capture column (5.0 cm ID×6.4 cm) of Fractogel® EMD TMAE-650 (S) resin (EM Separations, Gibbstown, N.J.) equilibrated in Buffer A. Following a wash with Buffer A, the antigen was eluted with a gradient of 0–1.0M NaCl in Buffer A. immuno-dot blotting was performed to determine which fractions from the column contained L1 protein.

Fractions containing L1 protein as determined by immunodot blot were assayed for total protein by the Bradford method followed by SDS-PAGE using silver staining and Western blotting.

TMAE fractions showing comparable purity and enrichment of L1 protein were pooled. The antigen was concentrated by ammonium sulfate fractionation. Samples were adjusted to 35% saturated ammonium sulfate by addition of solid reagent while gently stirring over 10 min. The samples were placed on ice and precipitation allowed to proceed for 5 hours. The samples were centrifuged at 12,000×g. The pellet was resuspended in 20.0 mL PBS (6.25 mM Na phosphate, pH 7.2, 150 mM NaCl).

Resuspended pellets were chromatographed separately on a L1 .size-exclusion column (2.6 cm ID×89 cm) of Sephacryl 500 HR resin (Pharmacia, Piscataway, N.J.). Running buffer was PBS. Fractions were analyzed by SDS-PAGE using silver staining and Western blot detection. The purest fractions were pooled. Resulting pools were concentrated in a 50 mL stirred cell using 43 mm YM-100 flat-sheet membranes (Amicon, Beverly, Mass.) at a N2 pressure of 4–6 psi.

Final product was analyzed by SDS-PAGE using colloidal Coomassie staining. The L1 protein was estimated to be 70% homogeneous. The identity of L1 was confirmed by Western blotting using the appropriate antisera. The final product was aliquoted and stored at −70° C. This process resulted in a total of 7.4 mg protein.

D. Analytical Procedures Immuno-Dot Blot Procedure

Samples were diluted (when necessary) 1:10 in Milli-Q-H₂O and 10 mcL of sample was spotted onto PolyScreen™ PVDF membranes (NEN Research Products, Boston, Mass.). After spots had dried, the membranes were washed in water and allowed to dry. Primary antibody solution was prepared by dilution of the appropriate antiser L1 um in blotting buffer (5% non-fat milk in 6.25 mM Na phosphate, pH 7.2, 150 mM NaCl, 0.02% NaN₃). Incubation was for at least 1 hour at 20°–23° C. The blot was washed for I min each in three changes of PBS (6.25 mM Na phosphate, pH 7.2, 150 mM NaCl). Secondary antibody solution was prepared by diluting the appropriate alkaline phosphatase-linked conjugate antiserum in blotting buffer. Incubation proceeded under the same conditions for at least 1 hour. Blots were washed as before and detected using a 1 step NBT/BCIP substrate (Pierce, Rockford, Ill.).

Antibodies used for detection were as follows:

HPV6a L1 I was detected by MAB 837 (Chemicon International, Inc., Temecula, Calif.). HPV 6a L2 was detected by mouse anti-HPV6a L2-trpE fusion serum pool # 641 and 647. HPV 16 L1 was detected by MAB 885 (Chemicon International, Inc., Temecula, Calif.). HPV 16 L2 was detected by mouse anti-HPV 16 L2-trpE fusion serum pool # 611.

Bradford Assay for Total Protein

Total protein was assayed using a commercially available Coomassie Plus® kit (Pierce, Rockford, Ill.). Samples were diluted to appropriate levels in Milli-Q-H20. Volumes required were 0.1 mL and 1.0 mL for the standard and microassay protocols, respectively. For both protocols, BSA (Pierce, Rockford, Ill.) was used to generate the standard curve. The assay was performed according to manufacturer's recommendations. Standard curves were plotted using CricketGraph® software on a Macintosh IIci computer.

EXAMPLE 35

Purification of Recombinant HPV Type 11 L1 Capsid Proteins

All steps were performed at 4° C. unless noted.

Cells were stored frozen at −70° C. Frozen cells (wet weight=180 g) were thawed at 20°–23° C. and resuspended in 900 mL "Breaking Buffer" (50 mM MOPS, pH 7.2, 500 mM NaCl, 1 mM CaCl₂). The protease inhibitors AEBSF and pepstatin A were added to final concentrations of 1 mM and 1.7 μM, respectively. The cell slurry was broken at a pressure of approximately 16,000 psi by 4 passes in a M110-Y Microfluidizer (Microfluidics Corp., Newton, Mass.). A sufficient volume of 10% Triton X100® detergent (Pierce, Rockford, Ill.) was added to the broken cell slurry to bring the concentration of TX100 to 0.5%. The slurry was stirred for 20 hours. The Triton X100-treated lysate was centrifuged at 12,000×g for 40 min to remove cellular debris. The supernatant liquid containing L1 protein was recovered.

The supernatant liquid was diafiltered against five volumes of 20 mM sodium phosphate, pH 7.2,0.5 M NaCl using a 300K tangential flow membrane cassette (Filtron, Northborough, Mass.). The material retained by the membrane was shown by radioimmunoassay and western blotting to contain the L1 protein.

The retentate was applied to a high resolution affinity column (11.0 cm ID×5.3 cm) of SP Spherodex (M)® resin (IBF, Villeneuve-la-Garenne, France) equilibrated in 20 mM sodium phosphate, pH 7.2, 0.5 M NaCl. Following a wash with equilibration buffer and a step wash with 20 mM sodium phosphate, pH 7.2, 1.0M NaCl, the L1 protein was eluted with a step wash of 20 mM sodium phosphate, pH 7.2, 2.5M NaCl. Fractions were collected during the washes and elution. Column fractions were assayed for total protein by the Bradford method. Fractions were then analyzed by Western blotting and SDS-PAGE with colloidal Coomassie detection. Fractions were also analyzed by radioimmunoassay.

SP Spherodex fractions showing comparable purity and enrichment of L1 protein were pooled.

Final product was analyzed by western blotting and SDS-PAGE with colloidal Coomassie detection. The L1 i protein was shown by L1-densitometry of the Coomassie-stained gels to be >90% homogeneous. The identity of L1 protein was confirmed by Western blotting. The final product was filtered aseptically through a 0.22 μm membrane and stored at 4° C. This process resulted in a total of 202 mg protein.

Electron microscopy analysis is performed by Structure Probe (West Chester, Pa.). An aliquot of sample is placed on a 200 mesh carbon-coated copper grid. A drop of 2% phosphotungstic acid, pH 7.0 is placed on the grid for 20 seconds. The grid is allowed to air dry prior to TEM examination. All microscopy is performed using a JEOL 100 CX transmission electron microscope (JEOL USA, Inc.) at an accelerating voltage of 100 kV. The micrographs generated have a final magnification of 100,000×.

SDS-PAGE and Western Blot Assays

All gels, buffers, and electrophoretic apparatus were obtained from Novex (San Diego, Calif.) and were run according to manufacturer's recommendations. Briefly, samples were diluted to equal protein concentrations in Milli-Q-$H_2O$ and mixed 1:1 with sample incubation buffer containing 200 mM DTT. Samples were incubated 15 min at 100° C. and loaded onto pre-cast 12% Tris-glycine gels. The samples were electrophoresed at 125V for 1 hr 45 min. Gels were developed by colloidal Coomassie staining using a commercially obtained kit (Integrated Separation Systems, Natick, Mass.).

For Western blots, proteins were transferred to PVDF membranes at 25V for 40 min. Membranes were washed with Milli-Q-$H_2O$ and air-dried. Primary antibody was polyclonal rabbit antiserum raised against a TrpE-HPV11L1 fusion protein (gift of Dr. D. Brown). The antibody solution was prepared by dilution of antiserum in blotting buffer (5% non-fat milk in 6.25 mM Na phosphate, pH 7.2, 150 mM NaCl, 0.02% $NaN_3$). Incubation was for at least 1 hour at 20°–23° C. The blot was washed for 1 min each in three changes of PBS (6.25 mM Na phosphate, pH 7.2, 150 mM NaCl). Secondary antibody solution was prepared by diluting goat anti-rabbit IgG alkaline phosphatase-linked conjugate antiserum (Pierce, Rockford, Ill.) in blotting buffer. Incubation proceeded under the same conditions for at least 1 hour. Blots were washed as before and detected using a 1 step NBT/BCIP substrate (Pierce, Rockford, Ill.).

EXAMPLE 36

Expression of HPV 18 L1 and L2 in Yeast

Plasmids p191-6 (pGAL1-10+HPV18 L1) and p195-11 (pGAL1-10+HPV18 L1+L2) were used to transform S. cerevisiae strain #1558 (MATa, leu2-04, prbl::HIS3, mnn9::URA3, adel, cir°). Clonal isolates were grown at 30° C. in YEHD medium containing 2% galactose for 88 hours. After harvesting the cells, the cell pellets were broken with glass beads and cell lysates analyzed for the expression of HPV18 L1 and/or HPV18 L2 protein by immunoblot analysis. Samples containing 25 μg of total cellular protein were electrophoresed through 10% Tris-Glycine gels (Novex, Inc.) under denaturing conditions and electroblotted onto nitrocellulose filters. L1 protein was immunodetected using rabbit antiserum raised against a trpE-HPV 11 L1 fusion protein as primary antibody (Brown et al., 1994, Virology 201:46–54) and horseradish peroxidase (HRP)-linked donkey anti-rabbit IgG (Amersham, Inc.) as secondary antibody. The filters were processed using the chemiluminescent ECL™ Detection Kit (Amersham, Inc.). A 50–55 KDa L1 protein band was detected in both the L1 and L1+L2 coexpressor yeast clones (strains 1725 and 1727, respectively) and not in the negative control (pGAL1-10 without L1 or L2 genes).

The HPV 18 L2 protein was detected by Western analysis using goat polyclonal antiserum raised against a trpE-HPV 18 L2 fusion protein as primary antibody followed by HRP-conjugated, rabbit anti-goat IgG (Kirkegaard and Perry Laboratories, Gaithersburg, Md.). The filters were processed as described above. The L2 protein was detected as a 75 kDa protein band in the L1+L2 coexpressor yeast clone (strain 1727) but not in either the negative control or the L1 expressor clone.

EXAMPLE 37

Fermentation of HPV 18 L1 (strain 1725) and 18 L1+AL2 (strain 1727)

Surface growth of a plate culture of strains 1725 and 1727 was aseptically transferred to a leucine-free liquid medium containing (per L): 8.5 g Difco yeast nitrogen base without amino acids and ammonium sulfate; 0.2 g adenine; 0.2 g uracil; 10 g succinic acid; 5 g ammonium sulfate; 40 g glucose; 0.25 g L-tyrosine; 0.1 g L-arginine; 0.3 g L-isoleucine; 0.05 g L-methionine; 0.2 g L-tryptophan; 0.05 g L-histidine; 0.2 g L-lysine; 0.3 g L-phenylalanine; this medium was adjusted to pH 5.0–5.3 with NaOH prior to sterilization. After growth at 28° C., 250 rpm on a rotary shaker, frozen culture vials were prepared by adding sterile glycerol to a final concentration of 17% (w/v) prior to storage at −70° C. (1 mL per cryovial). Inocula were developed in the same medium (500 mL per 2-L flask) and were started by transferring the thawed contents of a frozen culture vial and incubating at 28° C., 250 rpm on a rotary shaker for 29 hr. Fermentations of each strain used a New Brunswick SF-i 16 fermentor with a working volume of 10 L after inoculation. The production medium contained (per L): 20 g Difco yeast extract; 10 g Sheffield HySoy peptone; 20 g glucose; 20 g galactose; 0.3 mL Union Carbide UCON LB-625 antifoam; the medium was adjusted to pH 5.3 prior to sterilization. The entire contents (500 mL) of the 2-L inoculum flask was transferred to the fermentor which was incubated at 28° C., 5 L air per min, 400 rpm, 3.5 psi pressure. Agitation was increased as needed to maintain dissolved oxygen levels of greater than 40% of saturation. Progress of the fermentation was monitored by off-line glucose measurements (Beckman Glucose 2 Analyzer) and on-line mass spectrometry (Perkin-Elmer 1200). After incubation for 66 hr, cell densities of 9.5 to 9.7 g dry cell weight per L were reached. The cultures were concentrated by hollow fiber filtration (Amicon H5MP01-43 cartridge in an Amicon DC-10 filtration system) to ca. 2 L, diafiltered with 2 L phosphate-buffered saline, and concentrated further (to ca. 1 L) before dispensing into 500- L1 mL centrifuge bottles. Cell pellets were collected by centrifugation at 8,000 rpm (Sorval GS-3 rotor) for 20 min at 4° C. After decanting

EXAMPLE 38

Purification of Recombinant HPV Type 18 L1 Capsid Proteins

All steps performed at 4° C. unless noted.

Cells were stored frozen at −70° C. Frozen cells (wet weight=126 g) were thawed at 20°–23° C. and resuspended in 70 mL "Breaking Buffer" (20 mM sodium phosphate, pH 7.2, 100 mM NaCl). The protease inhibitors PMSF and pepstatin A were added to final concentrations of 2 mM and 1.7 µM, respectively. The cell slurry was broken at a pressure of approximately 16,000 psi by 4 passes in a M110-Y Microfluidizer (Microfluidics Corp., Newton, Mass.). The broken cell slurry was centrifuged at 12,000×g for 40 min to remove cellular debris. The supernatant liquid containing L1 antigen was recovered.

The supernatant liquid was diluted 1:5 by addition of Buffer A (20 mM MOPS, pH 7.0) and applied to an anion exchange capture column (9.0 cm ID×3.9 cm) of Fractogel L1 ( EMD TMAE-650 (M) resin (EM Separations, Gibbstown, N.J.) equilibrated in Buffer A. Following a wash with Buffer A, the antigen was eluted with a gradient of 0–1.0M NaCl in Buffer A. Column fractions were assayed for total protein by the Bradford method. Fractions were then analyzed at equal total protein loadings by Western blotting and SDS-PAGE with silver stain detection.

TMAE fractions showing comparable purity and enrichment of L1 protein were pooled. The antigen was concentrated by ammonium sulfate fractionation. The solution was adjusted to 35% saturated ammonium sulfate by adding solid reagent while gently stirring over 10 min. The sample was placed on ice and precipitation allowed to proceed for 4 hours. The sample was centrifuged at 16,000×g for 45 min. The pellet was resuspended in 20.0 mL PBS (6.25 mM Na phosphate, pH 7.2, 150 mM NaCl).

The resuspended pellet was chromatographed on a size exclusion column (2.6 cm ID×89 cm) of Sephacryl 500 HR resin (Pharmacia, Piscataway, N.J.). Running buffer was PBS. Fractions were analyzed by western blotting and SDS-PAGE with silver stain detection. The purest fractions were pooled. The resulting pool was concentrated in a 50 mL stirred cell using 43 mm YM-100 flat-sheet membranes (Amicon, Beverly, Mass.) at a N2 pressure of 4–6 psi.

Final product was analyzed by western blotting and SDS-PAGE with colloidal Coomassie detection. The L1 protein was estimated to be 50–60% homogeneous. The identity of L1 protein was confirmed by western blotting. The final product was aliquoted and stored at −70° C. This process resulted in a total of 12.5 mg protein.

EXAMPLE 39

Preparation of Immunogenic Compositions

Purified VLP are formulated according to known methods, such as by the admixture of pharmaceutically acceptable carriers, stabilizers, or a vaccine adjuvant. The immunogenic VLP of the present invention may be prepared for vaccine use by combining with a physiologically acceptable composition such as, e.g. PBS, saline or distilled water. The immunogenic VLP are administered in a dosage range of about 0.1 to 100 µg, preferably about 1 to about 20 µg, in order to obtain the desired immunogenic effect. The amount of VLP per formulation may vary according to a variety of factors, including but not limited to the individual's condition, weight, age and sex. Administration of the VLP formulation may be by a variety of routes, including but not limited to oral, subcutaneous, topical, mucosal and intramuscular. Such VLP formulations may be comprised of a single type of VLP (i.e., VLP from HPV6a) or a mixture of VLP (i.e, VLP from HPV6a, HPV11, HPV16 and HPV18).

An antimicrobial preservative, e.g. thimerosal, optionally may be present. The immunogenic antigens of the present invention may be employed, if desired, in combination with vaccine stabilizers and vaccine adjuvants. Typical stabilizers are specific compounds, e.g. polyanions such as heparin, inositol hexasulfate, sulfated beta-cyclodextrin, less specific excipients, e.g. amino acids, sorbitol, mannitol, xylitol, glycerol, sucrose, dextrose, trehalose, and variations in solution conditions, e.g. neutral pH, high ionic strength (ca. 0.5–2.0M salts), divalent cations ($Ca^{2+}$, $Mg^{2+}$). Examples of adjuvants are $Al(OH)_3$ and $Al(PO_4)$. The vaccine of the present invention may be stored under refrigeration or in lyophilized form.

EXAMPLE 40

Preparation of Antibodies to VLP

Purified VLP are used to generate antibodies. The term "antibody" as used herein includes both polyclonal and monoclonal antibodies as well as fragments thereof, such as Fv, Fab and F(ab)2 fragments that are capable of binding antigen or hapten. The antibodies are used in a variety of ways, including but not limited to the purification of recombinant VLP, the purification of native L1 I or L2 proteins, and kits. Kits would comprise a compartmentalized carrier suitable to hold in close confinement at least one container. The carrier would further comprise reagents such as the anti-VLP antibody or the VLP suitable for detecting HPV or fragments of HPV or antibodies to HPV. The carrier may also contain means for detection such as labeled antigen or enzyme substrates or the like. The antibodies or VLP or kits are useful for a variety of purposes, including but not limited to forensic analyses and epidemiological studies.

---

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 31 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

CTTAAAGCTT ATGTCACTTT CTCTTGTATC G                   31

( 2 ) INFORMATION FOR SEQ ID NO:2:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:2:

TGATAAGCTT GCTCAATGGT TCTCTTCCTC                      30

( 2 ) INFORMATION FOR SEQ ID NO:3:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:3:

TGGTCATCCC AAATCTTGAA A                               21

( 2 ) INFORMATION FOR SEQ ID NO:4:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:4:

CACCGTAGTG TTTGGAAGCG A                               21

( 2 ) INFORMATION FOR SEQ ID NO:5:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:5:

GAGGCTACCA GCGAGCCGGG C                               21

( 2 ) INFORMATION FOR SEQ ID NO:6:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:6:

GGCCAGTGGG CCAACAGGTT C 21

( 2 ) INFORMATION FOR SEQ ID NO:7:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:7:

CTCAGATCTC ACAAAACAAA ATGTGGCGGC CTAGCGACAG CACAG 45

( 2 ) INFORMATION FOR SEQ ID NO:8:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

GAGAGATCTT ACCTTTTAGT TTTGGCGCGC TTAC 34

( 2 ) INFORMATION FOR SEQ ID NO:9:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

TCCCCCGGGC ACAAAACAAA ATGGCACATA GTAGGGCCCG ACGAC 45

( 2 ) INFORMATION FOR SEQ ID NO:10:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

TCCCCCGGGC TAGGCCGCCA CATCTGAAAA AAATAAGG 38

( 2 ) INFORMATION FOR SEQ ID NO:11:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

GAAGATCTTC AAAACAAAAT GGCAGTGTGG CTGTCTAC 38

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GAAGATCTTT ATTAAGTACG TCTCTTGCGT TTAG        34

( 2 ) INFORMATION FOR SEQ ID NO:13:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GGAATTCACA AAACAAAATG GTTGCACGGT CACGAAAAC        39

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GGAATTCTTA TTCTGCGTAG ACAGCCACAC TG        32

( 2 ) INFORMATION FOR SEQ ID NO:15:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CTCAGATCTC ACAAAACAAA ATGTCTCTTT GGCTGCCTAT GTAGGCC        47

( 2 ) INFORMATION FOR SEQ ID NO:16:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GAGAGATCTT ACAGCTTACG TTTTTGCGT TTAGC        35

( 2 ) INFORMATION FOR SEQ ID NO:17:

( i ) SEQUENCE CHARACTERISTICS:
        ( A ) LENGTH: 45 base pairs

```
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

TCCCCCGGGC ACAAAACAAA ATGCGACACA AACGTTCTGC AAAAC                    45

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

TCCCCCGGGC TAGGCAGCCA AAGAGACATC TGA                                 33
```

What is claimed is:

1. A method of producing a human papillomavirus (HPV) vaccine for administration to humans comprising HPV vitrus-like particles (VLPs) comprising the steps of:
   (a) transforming a yeast with a DNA molecule, said DNA molecule encoding HPV L1 or HPV L1+L2 proteins to produce a transformed yeast cell;
   (b) cultivating the transformed cell under conditions that permit production of recombinant proteins and their spontaneous assembly into VLPs;
   (c) harvesting the VLPs from the transformed cell; and
   (d) purifying the VLPs by at least one chromatography step; and
   (e) preparing the vaccine.

2. A method according to claim 1 wherein the yeast is a strain of *Saccharomyces cerevisiae*.

3. A method according to claim 1 wherein the HPV is selected from the group consisting of HPV type 6a, HPV type 6b, 14PV type 11, HPV type 16, and HPV type 18.

* * * * *